US009664698B2

(12) United States Patent
Laaksonen et al.

(10) Patent No.: US 9,664,698 B2
(45) Date of Patent: *May 30, 2017

(54) BIOMARKERS FOR SENSITIVE DETECTION OF STATIN-INDUCED MUSCLE TOXICITY

(75) Inventors: Reijo Laaksonen, Lempaala (FI); Kim Ekroos, Espoo (FI); Reini Hurme, Espoo (FI); Minna Janis, Espoo (FI); Riikka Katainen, Espoo (FI); Kirill Tarasov, Espoo (FI)

(73) Assignee: ZORA BIOSCIENCES OY, Espoo (FI)

( * ) Notice: Subject to any disclaimer, the term of this patent is extended or adjusted under 35 U.S.C. 154(b) by 267 days.

This patent is subject to a terminal disclaimer.

(21) Appl. No.: 14/110,219

(22) PCT Filed: Apr. 8, 2011

(86) PCT No.: PCT/EP2011/055569
§ 371 (c)(1),
(2), (4) Date: Oct. 7, 2013

(87) PCT Pub. No.: WO2012/136272
PCT Pub. Date: Oct. 11, 2012

(65) Prior Publication Data
US 2014/0031332 A1    Jan. 30, 2014

(51) Int. Cl.
*G01N 33/92* (2006.01)
*A61B 5/00* (2006.01)
*G01N 30/72* (2006.01)
*G01N 30/88* (2006.01)

(52) U.S. Cl.
CPC .......... *G01N 33/92* (2013.01); *A61B 5/7275* (2013.01); *G01N 30/7233* (2013.01); *G01N 2030/8813* (2013.01); *G01N 2800/10* (2013.01); *G01N 2800/325* (2013.01); *G01N 2800/52* (2013.01)

(58) Field of Classification Search
None
See application file for complete search history.

(56) References Cited

U.S. PATENT DOCUMENTS

2008/0003684 A1* 1/2008 Laaksonen ........... C12Q 1/6883
436/63

FOREIGN PATENT DOCUMENTS

| CN | 1211184 A | 3/1999 |
|---|---|---|
| CN | 101189005 A | 5/2008 |
| JP | 2009-540314 A | 11/2009 |
| JP | 2010-500566 A | 1/2010 |
| WO | 97/29751 | 8/1997 |
| WO | 03/079026 | 9/2003 |
| WO | 03/079026 A1 | 9/2003 |
| WO | 2006/129859 A2 | 12/2006 |
| WO | 2007/061995 | 5/2007 |
| WO | 2007/061995 A2 | 5/2007 |
| WO | 2007/100782 A2 | 9/2007 |
| WO | 2007/127192 | 11/2007 |
| WO | 2007/127192 A2 | 11/2007 |
| WO | 2007/144467 | 12/2007 |
| WO | 2007/144467 A1 | 12/2007 |
| WO | 2007144467 A1 | 12/2007 |
| WO | 2008021192 A1 | 2/2008 |
| WO | 2010/108737 A1 | 9/2010 |

OTHER PUBLICATIONS

Japanese Examination Report dated Nov. 4, 2014, Japanese Application No. 2014-503005, pp. 1-3.
Laaksonen et al., "A Systems Biology Strategy Reveals Biological Pathways and Plasma Biomarker Candidates for Potentially Toxic Statin-Induced Changes in Muscle", PLOS ONE, Dec. 20, 2006, vol. 1, No. 1, pp. e97:1-9.
Laaksonen et al., "Lipidomics-Based Safety Biomarkers for Lipid-Lowering Treatments", Angiology, Apr. 1, 2008, vol. 59, No. 2, pp. 65S-68S.
Kaddurah-Daouk et al., "Lipidomic analysis of variation in response to simvastatin in the Cholesterol and Pharmacogenetics Study", Metabolomics, Jun. 1, 2010, vol. 6, No. 2, pp. 191-201.
Morandi et al., "High plasma creatine kinase: review of the literature and proposal for a diagnostic algorithm", Neurological Sciences; Nov. 1, 2006, vol. 27, No. 5, pp. 303-311.
Dolegowska et al., "Lipoxygenase-derived hydroxyeicosatetraenoic acids—novel perioperative markers of early post-transplant allografrt function?", Nephrology Dialysis Transplantation, Jun. 8, 2010, vol. 25, No. 12, pp. 4061-4067.
Gasper et al., "Creative kinase: a review of its use in the diagnosis of muscle disease", Medicine and Health, Nov. 1, 2005, vol. 88, No. 11, pp. 399-404.
Bjorn Oskarsson, "Myopathy: Five New Things", Neurology, Feb. 15, 2011, vol. 76, Issue 7, Supplement 2, pp. S14-S19.
Mammen et al., "Statin myopathy: a review of recent progress", Current Opinion in Rheumatology, Nov. 1, 2010, vol. 22, No. 6, pp. 644-650.
Extended European Search Report issued on Nov. 12, 2015 for European Patent Application No. 15171666.9, 20 pages.
Laaksonen, Reijo et al. A Systems Biology Strategy Reveals Biological Pathways and Plasma Bomarker Candidates for Potentially Toxic Statin-Induced Changes in Muscle, PLOS One Dec. 20, 2006, vol. 1, No. 1, pp. 1-9.

(Continued)

*Primary Examiner* — Theodore R West
(74) *Attorney, Agent, or Firm* — MH2 Technology Law Group, LLP

(57) ABSTRACT

The present invention inter alia provides a method, and uses thereof, of predicting statin-induced muscle toxicity or its complications, such as myalgia, myopathy and rhabdomyolysis, by detecting the lipid concentrations or lipid ratios of a biological sample and comparing it to a control. This method has identified lipid markers that are more specific and sensitive in detecting these statin-induced muscle toxicity than the currently utilized clinical markers. Also provided is an antibody towards said lipids, and the use thereof for predicting, diagnosing, statin-induced muscle toxicity. The invention additionally relates to kits comprising lipids and/or an antibody thereto, for use in the prediction and/or diagnosis of statin-induced muscle toxicity.

15 Claims, 3 Drawing Sheets

(56) References Cited

OTHER PUBLICATIONS

Laaksonen, Reijo et al. Lipidomics-Based Safety Biomarkers for Lipid-Lowering Treatments. Angiology, Apr. 1, 2008, vol. 59, No, 2, pp. 65S-68S.
Kaddurah-Daouk, Rima et al. Lipidomic analysis of variation in response to simvastatin in the Cholesterol and Pharmacogenetics Study. Metabolomics, Jun. 1, 2010, vol. 6, No. 2, pp. 191-201.
Morandi, L. et al. High plasma creatine kinase: review of the literature and proposal for a diagnostic algorithm. Neurological Sciences, Nov. 1, 2006, vol. 27, No. 5, pp. 303-311.
Dolegowska, Barbara et al. Lipoxygenase-derived hydroxyeicosatetraenoic acids-novel perioperative markers of early post-transplant allograft function? Nephrology Dialysis Transplantation, Jun. 8, 2010, vol. 25, No. 12, pp. 4061-4067.
International Preliminary Report on Patentability dated Jun. 24, 2013 from International Application No. PCT/EP2011/055569, pp. 1-23.
First Office Action and Search Report dated Nov. 27, 2014, Chinese Application No. 201180070668.8, pp. 1-15 (English Translation included).

\* cited by examiner

BIOMARKERS FOR SENSITIVE DETECTION OF STATIN-INDUCED MUSCLE TOXICITY

FIELD OF THE INVENTION

This invention relates to methods and uses involving lipid levels to predict or diagnose statin-induced muscle toxicity. The invention is applicable, inter alia, to determining whether a subject requires adjustment of statin treatment and to the evaluation of muscle toxicity induced by new lipid lowering drugs. The methods include analyzing lipid levels of a biological sample, and comparing it to a control.

BACKGROUND OF THE INVENTION

Statins are currently the most widely used lipid-lowering drugs because they reduce the incidence of hard cardiovascular end-points (cardiovascular death, myocardial infarction and stroke) by 25% to 35% in different patient populations. These populations include those with stable or unstable coronary artery disease, diabetics, and hypertensive patients with other risk factors. In general, statins are well tolerated although muscular, liver and gastrointestinal side effects can occur. Statins can be associated with a wide range of muscular side effects, from non-specific or atypical myalgias, to myopathy and the full-blown rhabdomyolysis syndrome.

Myalgias are defined as muscle pain or complaints of sore muscles that can either be generalized or localized. Such symptoms occur in up to 10% of patients and can force physicians to reduce dose, switch to another statin using a trial-and-error approach or stop the medication completely. These muscular symptoms can also contribute to the relatively high rate of patients stopping statin therapy within the first two years of the treatment. Thus, even the more benign muscular symptoms can have important consequences and limit the large clinical and socio-economic benefits potentially offered by these agents.

Myopathy, while less devastating than rhabdomyolysis, can also occur after treatment with statins and is defined as muscle pain and/or weakness with increased creatine kinase (CK) levels at least 10 times the upper limit of normal. The incidence of myopathy is approximately 1-5%. The known predisposing risk factors for statin-related muscle toxicity include renal insufficiency, hypothyroidism, hereditary or acquired muscle diseases, history of muscle toxicity with another statin or a fibrate, concomitant use of a fibric acid derivative, alcohol abuse, clinical settings where increased plasma levels of statins could occur, as well as Asian ancestry.

Rhabdomyolysis is a rare event (well below 0.1% of statin users) but constitutes a life-threatening condition characterized by severe muscle toxicity, large increase in plasma creatine kinase (CK) levels (exceeding 10,000 U/L) and renal insufficiency secondary to myoglobin toxicity. Rhabdomyolysis has caused several patient deaths and has led to the withdrawal of one statin from the market, cerivastatin, (Baycol, Bayer). The incidence of rhabdomyolysis was also recently shown to be increased with another HMG-CoA reductase inhibitor, simvastatin (Zocor, Merck & Co.), when administered at a high dose (A to Z trial).

Currently plasma/serum Creatine kinase (CK) measurement is used as a biomarker for statin-induced muscle toxicity. For the vast majority of cases, CK measurement remains uninformative despite the presence of symptoms. Plasma/serum CK is an unspecific marker because it can be elevated for many other reasons, including physical exercise. An even greater limitation is its poor sensitivity, since it becomes indicative only after a substantial damage to muscle cells involving CK leakage to plasma from tissues. Thus, to this end it is well justified to develop new biomarkers for diagnosis of statin-induced muscle toxicity. Earlier studies (Phillips PS et al.: "*Statin-associated myopathy with normal creatine kinase levels.*" Ann Intern Med. 2002 Oct. 1;137(7):581-5) on muscle specimens obtained from patients during acute muscle pain have demonstrated, e.g., an accumulation of inflammatory cells in histopathological studies.

The number of lipid mediators in the human body is overwhelming. Attempts have been made to facilitate their identification and quantification by advances in mass spectrometry and lipid biochemistry, which today enable the simultaneous high throughput identification and quantification of hundreds of molecular lipid species in several lipid classes (Ejsing C S, et al: *Global analysis of the yeast lipidome by quantitative shotgun mass spectrometry. Proc Natl Acad Sci USA* 2009, 106:2136-2141; Stahlman M, et al: *High-throughput shotgun lipidomics by quadrupole time-of-flight mass spectrometry. J Chromatogr B Analyt Technol Biomed Life Sci* 2009 Hiukka A, et al: *ApoCIII-enriched LDL in type 2 diabetes displays altered lipid composition, increased susceptibility for sphingomyelinase, and increased binding to biglycan. Diabetes* 2009, 58:2018-2026; Linden D, et al: *Liver-directed overexpression of mitochondrial glycerol-3-phosphate acyltransferase results in hepatic steatosis, increased triacylglycerol secretion and reduced fatty acid oxidation. FASEB J* 2006, 20:434-443.) collectively referred to as the lipidome. Lipidomic studies have sought to identify lipid cellular distribution and to describe their biochemical mechanisms, interactions and dynamics. Lipidomics is capable in principle of quantifying the exact chemical composition of lipidomes (Han X, Gross R W: *Global analyses of cellular lipidomes directly from crude extracts of biological samples by ESI mass spectrometry: a bridge to lipidomics. J Lipid Res* 2003, 44:1071-1079).

The bulk of the lipid data in the art today presents lipids in a sum composition format, i.e., phosphatidylcholine (PC) 34:1 (Brugger B, et al: *Quantitative analysis of biological membrane lipids at the low picomole level by nano-electrospray ionization tandem mass spectrometry. Proc Natl Acad Sci USA* 1997, 94:2339-2344) where the molecular lipid and the attached fatty acid tails remain unidentified. The identification of molecular lipid species, e.g., PC 16:0/18:1 (Ekroos K, et al: *Charting molecular composition of phosphatidylcholines by fatty acid scanning and ion trap MS3 fragmentation. J Lipid Res* 2003, 44:2181-2192) is the main feature of advanced lipidomics, which delivers highly resolved molecular lipid species rather than summed fatty acid information. For example, the information of the type of fatty acids and their positions of attachment to the glycerol backbone making up the particular PC molecule is revealed. There are conventional techniques such as thin-layer chromatography combined with gas chromatography but they not only require considerably larger sample amounts and laborious sample preparation, but they do not deliver the molecular lipid species. Despite multiple mass spectrometry techniques capable of characterizing lipid entities, most of them are still unable to deliver reliable high-quality quantitative data in terms of absolute or close-to absolute concentrations.

There is a need for specific and reliable methods for the detection and diagnosis of statin-induced muscle toxicity, as well as markers useful in this regard. There is also a need for improvements of existing treatment regimes with statins or lipid lowering drugs.

SUMMARY OF THE INVENTION

The present invention inter alia provides novel lipidomic markers for the detection and diagnosis of statin-induced muscle toxicity, such as statin-induced muscle toxicity associated with muscle disease, muscle dystrophy, myalgia, myositis, myopathy or rhabdomyolysis.

In one aspect of the present invention, methods, lipidomic markers, agents such as antibodies and kits are inter alia disclosed and/or claimed herein for detecting statin associated muscular side effects, from non-specific or atypical myalgias to myopathy and the full-blown rhabdomyolysis syndrome. Myalgias are defined as muscle pain or complaints of sore muscles that can either be generalized or localized. Myopathy, while less catastrophic than rhabdomyolysis, can also occur after treatment with statins and is defined as muscle pain and/or weakness with increased CK levels at least 10 times the upper limit of normal.

Methods according to the invention may, e.g., comprise the steps of: a) providing a biological sample from a subject being treated, to be treated, or having been treated with a statin; b) determining the concentration(s) of one or more lipid(s) and/or one or more lipid ratio(s) identified herein as useful lipidomic markers in accordance with the invention in said sample; and c) comparing said determined lipid concentration(s) and/or lipid ratio(s) to the corresponding lipid concentration(s) and/or lipid ratio(s) in a control.

The lipidomic markers of the present invention allow for sensitive detection of statin-induced muscle toxicity. It will be appreciated that the same applies to the complications of statin-induced muscle toxicity. This will facilitate improving patient care, lessening symptom development and suffering, and achieving decreased morbidity/mortality associated with statin side-effects. Thus, the lipidomic markers described and claimed herein allow for individual tailoring of drug intervention regarding patients treated, or to be treated, with statins. Also, the invention is applicable to animal experiments where statins and statin-like compounds are tested. The invention will inter alia allow a better safety assessment of novel lipid lowering medications to be made.

Accordingly, a method is inter alia provided herein for determining whether a subject is at risk to develop, or is suffering from statin-induced muscle toxicity and/or one or more of its complications, comprising determining in a sample from said subject the concentration(s) of one or more lipid(s), wherein (an) increased or decreased concentration(s) in said sample, when compared to a control, is (are) indicative of said subject suffering from said statin-induced muscle toxicity and/or said complication(s), wherein the one or more lipid(s) whose increase in concentration is (are) compared to the control is (are) selected from Table 2: 12-HETE, 15-HETE, 13-HODE, PE P-18:0/20:4, PE O-18:1/20:4, LacCer(d18:1/22:0), LacCer(d18:1/20:0), PE 18:0/20:4, Cer(d18:1/18:0), LacCer(d18:1/24:0), Cer(d18:1/20:0), PC16:0/20:3, AA, Cer(d18:1/24:1), Cer(d18:1/26:1), Glc/GalCer(d18:1/24:1), Cer(d18:1/22:0), Glc/GalCer(d18:1/18:0), Cer(d18:1/16:0), LacCer(d18:1/24:1), SM (d18:1/14:0) (d18:1/13:1—OH), LacCer(d18:1/16:0), CE 18:3 and PC 16:0/20:4; and wherein the one or more lipid(s) whose decrease in concentration is (are) compared to the control is (are) selected from the lipids in Table 2: 11_12-DHET, 14_15-DHET, 5-HETrE, 5-HETE and 8_9-DHET.

In a preferred embodiment, the one or more lipid(s) whose increase in concentration is (are) compared to the control is (are) selected from the lipids in Table 5: 12-HETE, 15-HETE, PE P-18:0/20:4, PE O-18:1/20:4, LacCer(d18:1/22:0) and Cer(d18:1/18:0).

In another preferred embodiment, the one or more lipid(s) whose decrease in concentration is (are) compared to the control is (are) selected from the lipids in Table 5: 5-HETE and 8_9-DHET.

In an alternative embodiment the present invention relates to a method for determining whether a subject is at risk to develop, or is suffering from statin-induced muscle toxicity and/or one or more of its complications, comprising determining in a sample from said subject one or more lipid ratio(s), wherein (an) increased or decreased lipid ratio(s) in said sample, when compared to a control, is (are) indicative of said subject suffering from said statin-induced muscle toxicity and/or said complication(s), wherein the one or more lipid ratio(s) whose increase is (are) compared to the control is (are) selected from the lipid ratios in Table 4: 12-HETE/5-HETrE, 12-HETE/8_9-DHET, 12-HETE/5-HETE , 12-HETE/14_15-DHET, 12-HETE/CE 20:4, 12-HETE/15-HETrE , 12-HETE/LPC 16:0, 15-HETE/8_9-DHET, 12-HETE/5-HEPE, 12-HETE/PC 18:0/18:2, 12-HETE/CK, 15-HETE/5-HETE, 12-HETE/CE 18:3, 13-HODE/8_9-DHET and 15-HETE/15-HETrE; and wherein the one or more lipid ratio(s) whose decrease is (are) compared to the control is (are) selected from the lipid ratios in Table 4: 11_12-DHET/CE 18:2, 14_15-DHET/CE 18:2, 11_12-DHET/LacCer(d18:1/24:0), 11_12-DHET/Cer(d18:1/16:0), 5-HETE/CE 20:4, 14_15-DHET/LacCer(d18:1/22:0), 14_15-DHET/Glc/GalCer(d18:1/18:0), 15-HETrE/LacCer(d18:1/22:0), 11_12-DHET/Cer(d18:1/20:0), 5-HETE/CE 18:2, 5-HETE/CE 18:1, 8_9-DHET/CE 18:2, 8_9-DHET/CE 18:1, 8_9-DHET/CE 22:6, 14_15-DHET/Cer(d18:1/18:0), 5-HETE/LacCer(d18:1/24:1), 8_9-DHET/CE 16:0, 5-HETE/Glc/GalCer(d18:1/18:0), 8_9-DHET/Cer(d18:1/26:0), 8_9-DHET/LacCer(d18:1/16:0), 5-HETE/9-HODE, 8_9-DHET/Cer(d18:1/16:0), 8_9-DHET/Cer(d18:1/26:1), 8_9-DHET/Glc/GalCer(d18:1/18:0), 11_12-DHET/12-HETE , 8_9-DHET/9-HODE , 5-HETE/Cer(d18:1/18:0), 8_9-DHET/AA, 5-HETE/PC 16:0/20:3, 8_9-DHET/Cer(d18:1/24:1), 8_9-DHET/CE 16:1, 11-HETE/12-HETE, 8_9-DHET/Cer(d18:1/20:0), 8_9-DHET/PC 16:0/20:3 and 8_9-DHET/Cer(d18:1/18:0).

In a preferred embodiment, the one or more lipid ratio(s) whose increase is (are) compared to the control is (are) selected from the lipid ratios in Table 6: 12-HETE/5-HETrE, 12-HETE/5-HETE, 12-HETE/CE 20:4, 12-HETE/15-HETrE, 12-HETE/LPC 16:0, 15-HETE/8_9-DHET, 12-HETE/CK, 13-HODE/8_9-DHET and 15-HETE/15-HETrE.

In another preferred embodiment, the one or more lipid ratio(s) whose decrease is (are) compared to the control is (are) selected from the lipid ratios in Table 6: 11_12-DHET/Cer(d18:1/16:0), 5-HETE/CE 18:2, 8_9-DHET/CE 18:1, 8_9-DHET/LacCer(d18:1/16:0), 5-HETE/9-HODE, 8_9-DHET/Glc/GalCer(d18:1/18:0), 5-HETE/Cer(d18:1/18:0), 8_9-DHET/Cer(d18:1/24:1), 11-HETE/12-HETE and 8_9-DHET/Cer(d18:1/18:0).

In yet another alternative embodiment the present invention relates to a method for determining whether a subject is at risk to develop, or is suffering from statin-induced muscle toxicity and/or one or more of its complications, comprising determining in a sample from said subject one or more lipid concentration(s) and one or more lipid ratio(s) of a lipid marker combination, wherein said lipid marker combination comprises at least one lipid of Tables 2, 5 or 7, and at least one lipid ratio of Tables 4 or 6, wherein (an) increased or decreased concentration(s) of said lipid(s) and/or an increase or decrease of said lipid ratio(s) in said sample, when compared to a control, are indicative of said subject suffering from said statin-induced muscle toxicity and/or said complication(s). The direction of change (decrease or increase) is indicated in Tables 2, 4, 5, 6 and 7.

In a preferred embodiment, the lipid concentrations determined in accordance with any of the methods of the invention are those of any of the lipid combinations identified in Table 7.

In another aspect, the present invention relates to a method for determining whether the statin treatment or the treatment with a lipid lowering drug of a subject needs adjustment, comprising determining in a sample from said subject the concentration(s) of one or more lipid(s), wherein (an) increased or decreased concentration(s) in said sample, when compared to a control, is (are) indicative of said treatment requiring adjustment, wherein the one or more lipid(s) whose increase in concentration is (are) compared to the control is (are) selected from the lipids in Table 2: 12-HETE, 15-HETE, 13-HODE, PE P-18:0/20:4, PE O-18:1/20:4, LacCer(d18:1/22:0), LacCer(d18:1/20:0), PE 18:0/20:4, Cer(d18:1/18:0), LacCer(d18:1/24:0), Cer(d18:1/20:0), PC16:0/20:3, AA, Cer(d18:1/24:1), Cer(d18:1/26:1), Glc/GalCer(d18:1/24:1), Cer(d18:1/22:0), Glc/GalCer(d18:1/18:0), Cer(d18:1/16:0), LacCer(d18:1/24:1), SM (d18:1/14:0) (d18:1/13:1-OH), LacCer(d18:1/16:0), CE 18:3 and PC 16:0/20:4; and wherein the one or more lipid(s) whose decrease in concentration is (are) compared to the control is (are) selected from the lipids in Table 2: 11_12-DHET, 14_15-DHET, 5-HETrE, 5-HETE and 8_9-DHET.

In a preferred embodiment, the one or more lipid(s) whose increase in concentration is (are) compared to the control is (are) selected from the lipids in Table 5: 12-HETE, 15-HETE, PE P-18:0/20:4, PE O-18:1/20:4, LacCer(d18:1/22:0) and Cer(d18:1/18:0).

In another preferred embodiment, the one or more lipid(s) whose decrease in concentration is (are) compared to the control is (are) selected from the lipids in Table 5: 5-HETE and 8_9-DHET.

In an alternative embodiment the present invention relates to a method for determining whether the statin treatment or the treatment with a lipid lowering drug of a subject needs adjustment, comprising determining in a sample from said subject one or more lipid ratio(s), wherein (an) increased or decreased lipid ratio(s) in said sample, when compared to a control, is (are) indicative of said treatment requiring adjustment, wherein the one or more lipid ratio(s) whose increase is (are) compared to the control is (are) selected from the lipid ratios in Table 4: 12-HETE/5-HETrE, 12-HETE/8_9-DHET, 12-HETE/5-HETE, 12-HETE/14_15-DHET, 12-HETE/CE 20:4, 12-HETE/15-HETrE, 12-HETE/LPC 16:0, 15-HETE/8_9-DHET, 12-HETE/5-HEPE, 12-HETE/PC 18:0/18:2, 12-HETE/CK, 15-HETE/5-HETE, 12-HETE/CE 18:3, 13-HODE/8_9-DHET and 15-HETE/15-HETrE; and wherein the one or more lipid ratio(s) whose decrease is (are) compared to the control is (are) selected from the lipid ratios in Table 4: 11_12-DHET/CE 18:2, 14_15-DHET/CE 18:2, 11_12-DHET/LacCer(d18:1/24:0), 11_12-DHET/Cer (d18:1/16:0), 5-HETE/CE 20:4, 14_15-DHET/LacCer(d18:1/22:0), 14_15-DHET/Glc/GalCer(d18:1/18:0), 15-HETrE/LacCer(d18:1/22:0), 11_12-DHET/Cer(d18:1/20:0), 5-HETE/CE 18:2, 5-HETE/CE 18:1, 8_9-DHET/CE 18:2, 8_9-DHET/CE 18:1, 8_9-DHET/CE 22:6, 14_15-DHET/Cer(d18:1/18:0), 5-HETE/LacCer(d18:1/24:1), 8_9-DHET/CE 16:0, 5-HETE/Glc/GalCer(d18:1/18:0), 8_9-DHET/Cer (d18:1/26:0), 8_9-DHET/LacCer(d18:1/16:0), 5-HETE/9-HODE, 8_9-HET/Cer(d18:1/16:0), 8_9-DHET/Cer(d18:1/26:1), 8_9-DHET/Glc/GalCer(d18:1/18:0), 11_12 -DHET/12-HETE, 8_9-DHET/9-HODE, 5 -HETE/Cer(d18:1/18:0), 8_9-DHET/AA, 5-HETE/PC 16:0/20:3, 8_9-DHET/Cer(d18:1/24:1), 8_9-DHET/CE 16:1, 11-HETE/12-HETE, 8_9-HET/Cer(d18:1/20:0), 8_9-DHET/PC 16:0/20:3 and 8_9-DHET/Cer(d18:1/18:0).

In a preferred embodiment, the one or more lipid ratio(s) whose increase is (are) compared to the control is (are) selected from the lipid ratios in Table 6: 12-HETE/5-HETrE, 12-HETE/5-HETE, 12-HETE/CE 20:4, 12-HETE/15-HETrE, 12-HETE/LPC 16:0, 15-HETE/8_9-DHET, 12-HETE/CK, 13-HODE/8_9-DHET and 15-HETE/15-HETrE.

In another preferred embodiment, the one or more lipid ratio(s) whose decrease is (are) compared to the control is (are) selected from the lipid ratios in Table 6: 11_12-DHET/Cer(d18:1/16:0), 5-HETE/CE 18:2, 8_9-DHET/CE 18:1, 8_9-DHET/LacCer(d18:1/16:0), 5-HETE/9-HODE, 8_9-DHET/Glc/GalCer(d18:1/18:0), 5-HETE/Cer(d18:1/18:0), 8_9-DHET/Cer(d18:1/24:1), 11-HETE/12-HETE and 8_9-DHET/Cer(d18:1/18:0).

Again, in a preferred embodiment, the lipid concentrations determined in accordance with any of the methods of the invention are those of any of the lipid combinations identified in Table 7.

In yet another alternative embodiment the present invention relates to method for determining whether the statin treatment or the treatment with a lipid lowering drug of a subject needs adjustment, comprising determining in a sample from said subject one or more lipid concentration(s) and one or more lipid ratio(s) of a lipid marker combination, wherein said lipid marker combination comprises at least one lipid of Tables 2, 5 or 7 and at least one lipid ratio of Tables 4 or 6, wherein (an) increased or decreased concentration(s) of said lipid(s) and/or an increase or decrease of said ratio(s) in said sample, when compared to a control, are indicative of said treatment requiring adjustment. Again, the direction of change (decrease or increase) is indicated in Tables 2, 4, 5, 6 and 7.

For the purpose of the method for determining whether the statin treatment or the treatment with a lipid lowering drug of a subject needs adjustment, the adjustment of said statin treatment may comprise (a) a reduction of statin dose; (b) a cessation of statin treatment; (c) a re-commencement of statin treatment; (d) a change to a different statin drug, (e) a change to a different lipid lowering drug, or (f) a cessation of another drug treatment which led to muscle toxicity due to its interaction with one or more statins.

In a further embodiment, the methods of the invention may be used for evaluating the degree of muscle toxicity induced by a novel statin or a novel lipid lowering medication in a subject undergoing treatment with said statin or lipid lowering medication.

The methods of the invention may be used for determining early warning signs of muscle toxicity in said subject.

In addition, or alternatively, the methods may be used for determining whether the symptoms of muscle toxicity found in a subject are due to statin-induced muscle toxicity.

For the purposes of the methods of the invention, at least one lipid concentration or lipid ratio from Tables 2, 4, 5, 6 or 7, or combinations thereof, may be determined to assess whether a subject is at risk to develop, or is suffering from statin-induced muscle toxicity and/or one or more of its complications, or to determine whether the statin treatment or treatment with a lipid lowering drug of a subject needs adjustment. However, it is also possible, and may be advantageous, to determine at least 2, at least 3, at least 4, at least 5, at least 6, at least 7, or at least 8 lipid concentrations or lipid ratios, or combinations thereof, from Tables 2, 4, 5, 6, or 7. Likewise, as mentioned earlier herein, it may be advantageous to determine the concentrations of the lipids in the lipid combinations identified in Table 7. It may also be useful to perform combinations of the aforementioned determinations, e.g., to determine the concentration of at least one lipid from Tables 2, 5 or 7 and further to determine at least one ratio from Tables 4 and 6. Where more than one lipidomic marker is determined and used for the assessment, it may be advantageous that a specific lipid concentration or lipid ratio, or a specific combination thereof, is given greater weight than others in the above-mentioned assessment.

The methods of the invention encompass the determination of (a) lipid concentrations or (a) lipid ratio(s) in a sample from a subject that is being treated with one or more statins.

Alternatively, the methods of the invention encompass the determination of (a) lipid concentration(s) or (a) lipid ratio(s) in a sample from a subject that had undergone statin treatment, but discontinued said treatment, e.g., due to onset of muscle pain.

In a further alternative, the methods of the invention encompass the determination of (a) lipid concentration(s) or (a) lipid ratio(s) in a sample from a subject that has not yet been treated with statins.

The methods of the invention may further encompass the determination of (a) lipid concentration(s) or (a) lipid ratio(s) in a sample from a subject that is at a high risk for developing statin-induced muscle toxicity and/or one or more of its complications.

For the purposes of the methods of the invention, a comparison of the subject's sample is made in respect of a control.

In a preferred embodiment, the control is, for example, a control sample, preferably a control sample that corresponds to the subject's sample.

In a preferred embodiment, the control sample is from the same subject undergoing statin treatment, but prior to the onset of muscle toxicity. The control may, however, also be a sample from the same subject prior to statin treatment or during discontinuation of statin treatment. In another preferred embodiment, it may also be from another subject with no signs or history of statin-induced muscle toxicity.

In another preferred embodiment, the control is a control sample from a population of subjects with no signs or history of statin-induced muscle toxicity.

In yet another preferred embodiment, however, the control is not a sample but merely a control value established from one or more subject(s) not on statin treatment and with no signs or history of muscle toxicity. Alternatively, the control may advantageously be a control value established from one or more subject(s) on statin treatment and with no signs or history of muscle toxicity.

In accordance with the present invention, the concentration(s) of the individual lipid(s) or the lipid ratio(s) in the sample from the subject are preferably compared to the concentration(s) of the corresponding lipid(s) or the corresponding lipid ratio(s) in the control, be it a control sample or a control value, for determining whether a subject is at risk to develop, or is suffering from statin-induced muscle toxicity (and/or one or more of its complications), or to determine whether the statin treatment or treatment with a lipid lowering drug of a subject needs adjustment. Some illustrative examples of the comparisons that can be made between a subject's sample and a control are shown in the table below:

| | Comparison pairs | | |
|---|---|---|---|
| | Case | Control | Readout |
| 1 | Subject on Statin with muscle toxicity or a high risk subject on statin with no muscle toxicity | Subject(s) on Statin with no muscle toxicity | Increase or decrease in concentration of lipids or ratios in Tables 2 and 4, or in the concentrations of the lipids of the combinations in Table 7 |
| 2 | Subject on Statin with muscle toxicity | Same subject on statin prior to muscle toxicity | Increase or decrease in concentration of lipids or ratios in Tables 2 and 4, or in the concentrations of the lipids of the combinations in Table 7 |
| 3 | Subject on Statin with muscle toxicity | Same subject prior to statin therapy | Change or lack of change in concentration of lipids or ratios in Tables 2 and 4, or in the concentrations of the lipids of the combinations in Table 7, e.g., a) increased concentration of 12-HETE, 15-HETE, 13-HODE (Table 2), b) decreased concentration of "decreased" lipids in Table 2 and c) lack of change in remaining lipids in Table 2 |
| 4 | Subject on statin with muscle toxicity | Same subject after statin withdrawal | Change or lack of change in concentration of lipids or ratios in Tables 2 and 4, or in the concentrations of the lipids of the combinations in Table 7, e.g., a) increased concentration of 12-HETE, 15-HETE, 13-HODE (Table 2), b) decreased concentration of "decreased" lipids in Table 2 and c) lack of change in remaining lipids in Table 2 |

On the other hand, the comparison in accordance with the present invention of the concentration(s) of the individual lipid(s) or the lipid ratio(s) in the sample from said subject may also be made to the concentration(s) or the ratio(s) of (an)other individual molecule(s) or molecule ratio(s) in the control, again either control sample or control value, for determining whether a subject is at risk to develop, or is suffering from statin-induced muscle toxicity (and/or one or more of its complications), or to determine whether the statin treatment or treatment with a lipid lowering drug of a subject needs adjustment. Such other individual molecule(s) or molecule ratio(s) in the control is (are) preferably molecule(s) or (a) ratio(s) where the concentration(s) thereof or the ratio(s) is (are) similar, or essentially similar, in all or at least a majority of subjects, so that the concentration(s) or the ratio(s) is (are) suitable as point of reference for determining whether there is an increase or decrease in said sample in respect of the lipidomic markers according to the invention. Preferred in this regard is/are, for example, (an) other lipid(s) or (an)other lipid ratio(s). Also preferred in this regard is/are, for example, (a) protein(s) or (a) protein ratio(s). Particularly preferred in this regard is/are (a) molecule(s) or (a) molecule ratio(s) in the control that is/are regularly measured in a clinical setting. For example, preferred are embodiments where the comparison is made to the concentration of apoA, apoB, albumin or total PC in the control (again control sample or control value), or combinations thereof.

In a further embodiment, the methods of the invention may further comprise determining or evaluating the level of creatine kinase (CK) in the subject or in a sample from the subject. In one embodiment of the invention, the subject has elevated creatine kinase levels. In another embodiment of the invention, the subject does not have elevated creatine kinase levels.

In accordance with the methods of the invention, the sample can be blood plasma, blood serum, or muscle biopsy tissue. The sample may also be a fraction of blood, blood plasma or blood serum, e.g., a lipoprotein fraction. A blood sample can be prepared and plasma or serum, or fractions thereof, can be separated therefrom with techniques well known to the person skilled in the art. Alternatively, both the sample from the subject and the control sample may also be a tissue sample, e.g., muscle biopsy tissue.

Collecting information on a lipidomic marker (i.e., a lipid, lipid concentration, lipid ratio, or lipidomic marker combination as described and claimed herein) according to the methods of the present invention from the subject's sample, and also from the control sample, can be performed via various chemical and high resolution analytical techniques. Particularly suitable analytical techniques include, but are not limited to, mass spectrometry and nuclear magnetic resonance spectroscopy. Indeed, any high resolution technique capable of resolving individual lipids or lipid classes and providing structural information of the same can be used to determine the lipidomic markers according to the invention from the subject's sample, and also from the control sample. For the purposes of the methods of the present invention the lipid concentration(s) or lipid ratio(s) are thus preferably determined by using mass spectrometry. However, nuclear magnetic resonance spectroscopy, fluorescence spectroscopy or dual polarisation interferometry, high performance separation methods such as HPLC or UPLC, an immunoassay such as an ELISA and/or the use of a binding moiety capable of specifically binding the lipid analyte are also useful in this regard.

As indicated above, according to an alternative or further embodiment of the methods of the invention, a lipid analyte in a sample can be detected and/or quantified by combining the analyte with a binding moiety capable of specifically binding the analyte. The binding moiety can include, for example, a member of a ligand-receptor pair, i.e., a pair of molecules capable of having a specific binding interaction. The binding moiety can also include, for example, a member of a specific binding pair, such as antibody-antigen, enzyme-substrate, nucleic acid-based ligands, other protein ligands, or other specific binding pairs known in the art.

In a particularly preferred embodiment, the lipidomic markers of the present invention are determined with mass spectrometry (MS), wherein the MS instrument is optionally coupled to direct infusion methods and high performance separation methods such as HPLC or UPLC. The amount of the individual lipids or lipid classes in the collected lipidomic markers is used when comparing the collected lipid profile to a control.

In another aspect of the present invention, an antibody against any one of the lipids in Tables 2, 3, 5 or 7 or against any one of the lipids in the lipid ratios in Tables 4 or 6 is used for predicting, diagnosing, preventing or treating statin-induced muscle toxicity and/or one or more of its complications in a subject. Similarly, the present invention relates to a method of predicting, diagnosing, preventing or treating statin-induced muscle toxicity and/or one or more of its complications in a subject using, or administering a therapeutically effective amount of, an antibody against any one of the lipids in Tables 2, 3, 5 or 7 or against any one of the lipids in the lipid ratios in Tables 4 or 6.

Also encompassed by the present invention is a kit for predicting statin-induced muscle toxicity and/or one or more of its complications, or for performing the methods or uses described and/or claimed herein, wherein the kit comprises: (a) a lipid standard chosen from the lipids in Tables 2, 3, 5 or 7 or the lipids in the lipid ratios in Tables 4 or 6; (b) one or more control markers (for example, a lipid or lipids, preferably a lipid corresponding to any of the lipidomic markers described and/or claimed herein, or another lipid(s), e.g., total PC, or another molecule, e.g., a protein, such as apoA, apoB or albumin); and optionally (c) an antibody or other binding moiety capable of binding any one of the lipids in Tables 2, 3, 5 or 7 or to any one of the lipids in the lipid ratios in Tables 4 or 6; and/or (d) reagents for performing said methods or uses. In a preferred embodiment, the kit is used to predict statin-induced muscle toxicity and/or one or more of its complications, or to perform any of the methods encompassed by the present invention, wherein the lipid concentration(s) or lipid ratio(s) in a sample from a subject is (are) determined by using mass spectrometry using mass spectrometry. The one or more control marker(s) of the kit of the present invention may be, for example, (a) lipid(s) or (a) protein(s). One preferred embodiment is wherein the one or more control marker(s) of the claimed kit is/are (a) molecule(s) that is/are regularly measured in a clinical setting. For example, preferred are embodiments wherein the one or more said control marker(s) is apoA, apoB, albumin or total PC, or a combination thereof.

In another aspect, the present invention relates to a statin or a lipid lowering drug for use in the treatment of a subject at risk to develop or suffering from atherosclerosis or cardiovascular disease (CVD) and/or one or more of their complications, wherein said subject would be identified as being at risk to develop or as suffering from statin-induced muscle toxicity when applying any of the methods, antibodies, kits or uses described and/or claimed herein. Similarly, the present invention relates to a method of treating a subject at risk to develop or suffering from atherosclerosis or cardiovascular disease (CVD) and/or one or more of their complications with a statin or a lipid lowering drug, wherein said subject would be identified as being at risk to develop or as suffering from statin-induced muscle toxicity when applying any of the methods, antibodies, kits or uses described and/or claimed herein.

In a further embodiment, the present invention relates to a statin or a lipid lowering drug for use in the treatment of a subject at risk to develop or suffering from atherosclerosis or cardiovascular disease (CVD) and/or one or more of their complications, wherein said subject actually has been identified as being at risk to develop or as suffering from statin-induced muscle toxicity by any of the methods, antibodies, kits or uses described and/or claimed herein. Similarly, the present invention relates to a method of treating a subject at risk to develop or suffering from atherosclerosis or cardiovascular disease (CVD) and/or one or more of their complications with a statin or a lipid lowering drug, wherein said subject actually has been identified as being at risk to develop or as suffering from statin-induced muscle toxicity by any of the methods, antibodies, kits or uses described and/or claimed herein.

In yet another aspect, the present invention relates to a statin or a lipid lowering drug for use in the treatment of a subject at risk to develop or suffering from atherosclerosis or cardiovascular disease (CVD) and/or one or more of their complications, wherein said subject would be identified as not being at risk to develop or as not suffering from statin-induced muscle toxicity when applying any of the methods, antibodies, kits or uses described and/or claimed herein. Similarly, the present invention relates to a method of treating a subject at risk to develop or suffering from atherosclerosis or cardiovascular disease (CVD) and/or one or more of their complications with a statin or a lipid lowering drug, wherein said subject would be identified as not being at risk to develop or as not suffering from statin-induced muscle toxicity when applying any of the methods, antibodies, kits or uses described and/or claimed herein.

In a further embodiment, the present invention relates to a statin or a lipid lowering drug for use in the treatment of a subject at risk to develop or suffering from atherosclerosis or cardiovascular disease (CVD) and/or one or more of their complications, wherein said subject actually has been identified as not being at risk to develop or as not suffering from statin-induced muscle toxicity by any of the methods, antibodies, kits or uses described and/or claimed herein. Similarly, the present invention relates to a method of treating a subject at risk to develop or suffering from atherosclerosis or cardiovascular disease (CVD) and/or one or more of their complications with a statin or a lipid lowering drug, wherein said subject actually has been identified as not being at risk to develop or as not suffering from statin-induced muscle toxicity by any of the methods, antibodies, kits or uses described and/or claimed herein.

In yet another aspect, the present invention relates to a statin or a lipid lowering drug for use in the treatment of a subject at risk to develop or suffering from atherosclerosis or cardiovascular disease (CVD) and/or one or more of their complications, wherein said treatment is, or has been, assessed using any of the methods for determining the need for treatment adjustment described and/or claimed herein, and wherein said treatment is, or has been, adjusted accordingly. Similarly, the present invention relates to a method of treating a subject at risk to develop or suffering from atherosclerosis or cardiovascular disease (CVD) and/or one or more of their complications with a statin or a lipid lowering drug, wherein said treatment is, or has been, assessed using any of the methods for determining the need for treatment adjustment described and/or claimed herein, and wherein optionally, said treatment is, or has been, adjusted accordingly. In connection with this aspect of the invention, such adjustment may suitably comprise, but is not limited to: (a) a reduction of statin dose; (b) a cessation of statin treatment; (c) a re-commencement of statin treatment; (d) a change to a different statin drug; (e) a change to a different lipid lowering drug; or (f) a cessation of another drug treatment which led to muscle toxicity due to its interaction with one or more statins.

In the context of all aspects and embodiments of the invention described and claimed herein, a statin may be one selected from, but not limited to, the group consisting of atorvastatin, cerivastatin, fluvastatin, fluvastatin XL, lovastatin, pitavastatin, pravastatin, rosuvastatin and/or simvastatin.

In the context of all aspects and embodiments of the invention described and claimed herein, the determination of the lipid concentration(s) or the lipid ratio(s) is typically performed using an assay.

In the context of all aspects and embodiments of the invention described and claimed herein, muscle toxicity may be associated with a muscle disease, for example, a muscle dystrophy.

In the context of all aspects and embodiments of the invention described and claimed herein, statin-induced muscle toxicity complications include in particular those selected from myalgia, myositis, myopathy and rhabdomyolysis. Statin myopathy or myositis is typically characterized by muscle pain (myalgia), muscle weakness, joint pain or rhabdomyolysis.

DETAILED DESCRIPTION OF THE INVENTION

Figure 1:
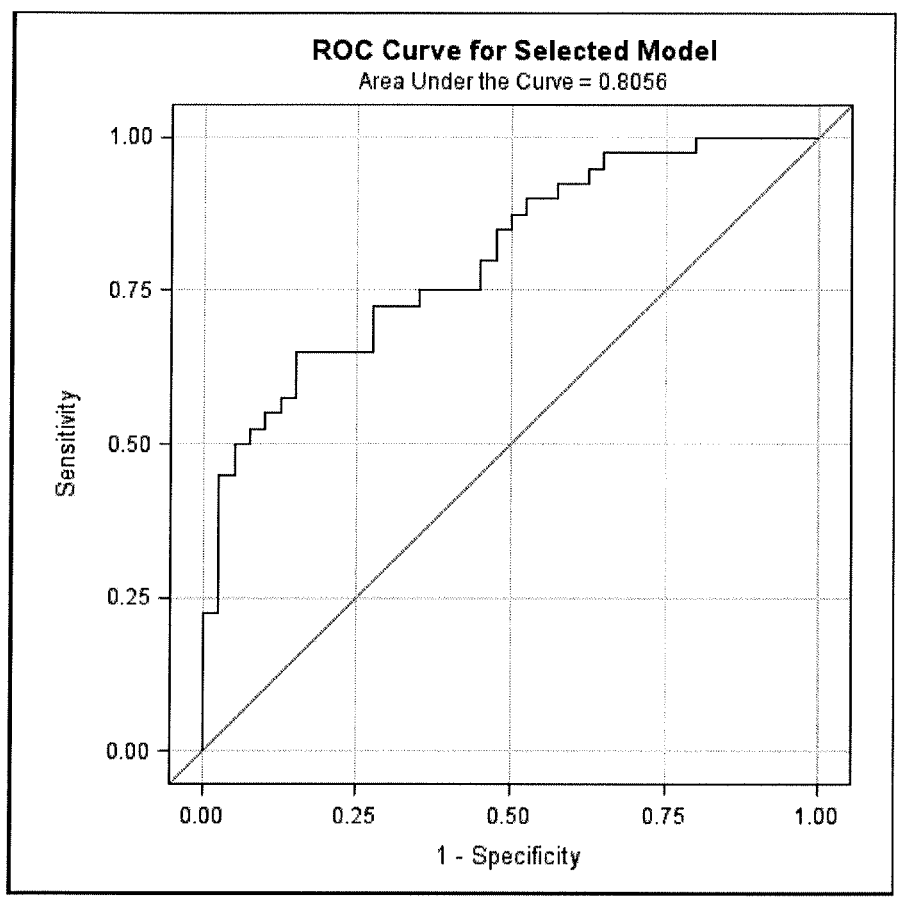
FIG. 1. ROC curve of two significant lipids, 8_9-DHET and 15-HETE, separating the cases and controls.

The present invention is the result of applying lipidomics to the identification of biomarkers indicative of statin-induced muscle toxicity. It will facilitate the mission of making sure the right individual receives the right statin or cholesterol lowering drug at the right time and dose, thereby opening this therapeutic area towards personalizing hitherto more generally applied medicines and/or treatment regimes.

Due to both high sensitivity and specificity of lipidomics, even the smallest sample amounts can be analyzed.

According to the present invention, the lipids and lipid ratios may be analyzed by a variety of techniques. In the context of the present invention, electrospray ionization mass spectrometry-based lipidomics is the preferred technology. The superior quality and specificity of shotgun and targeted analysis methods will meet stringent regulatory standards, such as good laboratory practice guidelines (GLP) when set-up in the proper environment.

As used herein, muscle toxicity is an adverse change in muscle cell(s) and/or muscle tissue induced by a drug.

As used herein, myopathy is a general term referring to any disease of muscles; myopathies can be acquired or inherited and can occur at birth or later in life (Source: NINDS Myopathy Page-http://accessible.ninds.nih.gov/health_and_medical/disorders/myopathy.htm).

As used herein, myalgia is a term that describes muscle ache or weakness without creatine kinase (CK) elevation.

As used herein, myositis is a term to describe muscle symptoms with increased CK levels.

Rhabdomyolysis as used herein is characterized by muscle symptoms with marked CK elevation (typically substantially greater than 10 times the upper limit of normal [ULN]) and with creatinine elevation (usually with brown urine and urinary myoglobin).

A muscle disease as used herein is any disease or disorder that affects the muscle system.

A muscle dystrophy as used herein is a hereditary muscle disease that weakens the muscles. Muscular dystrophies are characterized by progressive skeletal muscle weakness, defects in muscle proteins, and the death of muscle cells and tissue. Muscle dystrophies may include Duchenne, Becker, limb girdle, congenital, facioscapulohumeral, myotonic, oculopharyngeal, distal, and/or Emery-Dreifuss diseases.

As used herein, a complication of atherosclerosis or CVD includes in particular a complication selected from myocardial infarction (MI), AMI, angina pectoris, transient ischemic attack (TIA), stroke and death.

Some abbreviations used herein have the following meaning: CK is creatine kinase, ADR is adverse drug reaction, MS is mass spectrometry, HPLC is high performance liquid chromatography, and UPLC is ultra high performance liquid chromatography, ROC is receiving operating characteristics, and AUC is area under curve.

Moderate to severe creatine kinase elevations are those considered greater than 10 times ULN or greater than 10,000 IU/L. Mild CK elevation is considered to be greater than the ULN but less than 10 times the ULN (Jacobson T A, et al: *Toward "Pain-Free" Statin Prescribing: Clinical Algorithm for Diagnosis and Management of Myalgia. Mayo Clin Proc.* June 2008; 83(6):687-700; Joy T R and Hegele R A, *Narrative review: statin-related myopathy. Ann Intern Med.* 2009 Jun. 16;150(12):858-68).

A statin and a statin treatment, respectively, in accordance with the present invention will preferably be the following statins and treatments therewith, respectively: cerivastin (0.4 mg/d, Phillips PS et al: *Statin-Associated Myopathy with Normal Creatine Kinase Levels. Ann Intern Med.* 2002;137:581-585; Evans M and Rees A: *The myotoxicity of statins. Current Opinion in Lipidology.* 2002, 13:415-420); fluvastatin (80 mg/d, Jacobson T A, et al: *Toward "Pain-Free" Statin Prescribing:Clinical Algorithm for Diagnosis and Management of Myalgia. Mayo Clin Proc.* June 2008; 83(6):687-700); fluvastatin XL (80 mg/d, Jacobson T A, et al: *Toward "Pain-Free" Statin Prescribing:Clinical Algorithm for Diagnosis and Management of Myalgia. Mayo Clin Proc. June* 2008; 83(6):687-700); lovastatin (40 mg/d, Phillips P S et al: Statin-Associated Myopathy with Normal Creatine Kinase Levels. Ann Intern Med. 2002;137:581-585); pravastatin (40 mg/d, Phillips P S et al: *Statin-Associated Myopathy with Normal Creatine Kinase Levels. Ann Intern Med.* 2002;137:581-585; Jacobson T A, et al: *Toward "Pain-Free" Statin Prescribing:Clinical Algorithm for Diagnosis and Management of Myalgia. Mayo Clin Proc.* June 2008; 83(6):687-700); rosuvastatin (2.5 to 20 mg, 1 to 7 times weekly, with a preferred embodiment of 5 or 10 mg per day, Joy T R and Hegele R A, *Narrative review: statin-related myopathy. Ann Intern Med.* 2009 Jun. 16;150 (12):858-68); Jacobson T A, et al: *Toward "Pain-Free" Statin Prescribing:Clinical Algorithm for Diagnosis and Management of Myalgia. Mayo Clin Proc.* June 2008; 83(6):687-700); atorvasatin (10 or 20 mg/d, Phillips P S et al: *Statin-Associated Myopathy with Normal Creatine Kinase Levels. Ann Intern Med.* 2002;137:581-585); 40 mg/d (Laaksonen R, et al: *A Systems Biology Strategy Reveals Biological Pathways and Plasma Biomarker Candidates for Potentially Toxic Statin-Induced Changes in Muscle.* PLoS ONE. December 2006, Issue 1, e97: 1-9); 40 or 80 mg/d (Jacobson T A, et al: *Toward "Pain-Free" Statin Prescribing:Clinical Algorithm for Diagnosis and Management of Myalgia. Mayo Clin Proc.* June 2008; 83(6):687-700); and/or simvastatin (40 or 80 mg/d, Phillips P S et al: *Statin-Associated Myopathy with Normal Creatine Kinase Levels. Ann Intern Med.* 2002;137:581-585); 80 mg/d (Laaksonen R, et al: *A Systems Biology Strategy Reveals Biological Pathways and Plasma Biomarker Candidates for Potentially Toxic Statin-Induced Changes in Muscle.* PLoS ONE. December 2006, Issue 1, e97: 1-9; Jacobson T A, et al: *Toward "Pain-Free" Statin Prescribing: Clinical Algorithm for Diagnosis and Management of Myalgia. Mayo Clin Proc.* June 2008; 83(6):687-700). Alternatively, fluvastatin, lovastatin, pravastatin, rosuvastatin, atorvasatin and/or simvastatin may be administered at 40 mg/d (Jacobson T A, et al: *Toward "Pain-Free" Statin Prescribing:Clinical Algorithm for Diagnosis and Management of Myalgia. Mayo Clin Proc.* June 2008; 83(6):687-700). This treatment may or may not also comprise the administration of a fibrate or ezetimibe (10 mg/d, Jacobson T A, et al: *Toward "Pain-Free" Statin Prescribing: Clinical Algorithm for Diagnosis and Management of Myalgia. Mayo Clin Proc.* June 2008; 83(6):687-700). Colesevelam may be additionally administered with ezetimibe at a dosage of 3.75 g/d (Joy T R and Hegele R A, *Narrative review: statin-related myopathy. Ann Intern Med.* 2009 Jun. 16;150(12):858-68).

For the purposes of the present invention, a lipid lowering drug or medication is preferably an HMG-CoA reductase inhibitor, niacin (nicotinic acid), a cholesterol absorption inhibitor, a cholesteryl ester transfer protein (CETP) inhibitor, a bile acid sequestrant; a fibrate or a phytosterol.

For the purposes of the present invention, a cholesterol absorption inhibitor is preferably ezetimibe or SCH-48461; a cholesteryl ester transfer protein (CETP) inhibitor is preferably torcetrapib, anacetrapib or dalcetrapib; a bile acid sequestrant is preferably colesevelam, cholestyramine or colestipol; and a fibrate is preferably fenofibrate, gemfibrozil, clofibrate, or bezafibrate.

As used herein, a subject includes all mammals, including without limitation humans, but also non-human primates, dogs, cats, horses, sheep, goats, cows, rabbits, pigs and rodents. A particularly preferred subject in accordance with the present invention is a human.

As used herein a high risk subject is typically a subject, particularly a human, on high statin dose and/or on multiple medications (causing a risk for drug interactions), having a known muscle disease, or having a disease that may increase the risk of adverse events (e.g., hypothyroidism, renal insufficiency or a liver disease).

As used herein, a control may be a control sample or merely a control value. In case it is a control value, it will be appreciated that it may have already been determined, calculated or extrapolated prior to initiating the methods of the invention. Alternatively, the control value may be determined, calculated or extrapolated after conducting the determination of the concentration(s) of said one or more lipid(s) or said one or more lipid ratio(s) in accordance with the methods of the present invention. Thus, it will be appreciated that a suitable control value in accordance with the present invention may well be one that is taken from the literature.

A sample as used herein is defined as any biological sample obtained from a subject or a group or population of subjects. For the purposes of the present invention, the biological sample may be whole blood, blood serum, or blood plasma, with blood serum and blood plasma being preferred. Taking a blood sample of a patient is a part of normal clinical practice. The blood sample can be taken in connection with e.g. measuring the cholesterol levels in the patients. The collected blood sample can be prepared and serum or plasma can be separated with techniques well known to a person skilled in the art. Venous blood samples can be collected from patients using a needle and a BD Vacutainer® Plastic Tubes or Vacutainer® Plus Plastic Tubes (BD Vacutainer® SST™ Tubes contain spray-coated silia and a polymer gel for serum separation). Serum can be separated by centrifugation at 1300 RCF for 10 min at room temperature and stored in small plastic tubes at −80° C. The sample may also be a fraction of whole blood, blood plasma or blood serum, e.g., a lipoprotein fraction. In another preferred embodiment, the sample may also be a tissue sample, e.g., muscle biopsy tissue.

The lipids or other molecules in the control to which the comparison is made in accordance with the present invention are referred to herein also as control markers.

As used herein, the reference to a control sample from the same subject or from a(nother) subject may mean that the control sample has been directly obtained from said subject. Alternatively, however, it may also mean that it has been obtained as the result of a physical or chemical treatment of a sample directly obtained or taken from said subject, such as centrifugation, fractionation, enzymatic digestion, precipitation, and the like. The same applies to any reference herein to a control sample from a group of subjects or from a population of subjects.

The terms control sample from a group of subjects or control sample from a population of subjects as used herein furthermore preferably entail that the control sample is representative of said group or population. In this context, representative shall mean that the concentration(s) of the one or more lipids in said control sample to which a comparison is made in the context of the present invention corresponds to the average concentration(s) of said lipid(s) in corresponding individual samples from the subjects of said group or population. Preferably, the concentrations of all lipids in said control sample correspond to the average concentrations of said lipids in corresponding individual samples from the subjects of said group or population. Likewise, where a comparison is made in the context of the present invention to one or more other molecules, e.g., other lipids or proteins, such as total PC, or apoA, apoB, or albumin, respectively, a representative control sample is one where the concentration(s) of this (these) molecule(s) corresponds to the average concentration(s) of said molecule(s) in corresponding individual samples from the subjects of said group or population. In a preferred embodiment, a control sample from a group of subjects or a control sample from a population of subjects in the sense of the present invention is obtained by mixing equal amounts of samples directly obtained or taken from the subjects of said group or population, or by mixing equal amounts of fractions, constituents or reaction products (e.g., enzymatic reaction products or precipitates) thereof.

As used herein a control sample corresponds to the subject's sample if it has been obtained from the same type of biological tissue or source in the same, or essentially the same, manner. For example, if the subject's sample is a whole blood, blood plasma or blood serum sample, or a fraction thereof, a corresponding control sample will likewise be a whole blood, blood plasma or blood serum sample, or a fraction thereof, respectively. It will be appreciated that such corresponding control sample would include whole blood, blood plasma or blood serum samples, or fractions thereof, obtained by mixing the whole blood, blood plasma or blood serum samples, or certain fractions thereof, from a group or population of subjects (see also the further explanations herein and the claims regarding suitable control samples in accordance with the invention). The same applies mutatis mutandis to, e.g., tissue samples.

A lipid as used herein is defined as hydrophobic or amphiphilic small molecule.

For the purposes of the present invention, lipids are referred to according to the following nomenclature: CE is cholesteryl ester, Cer is ceramide, DAG is diacylglycerol, PC O is ether-linked PC, GD is disialogangliosides, GlcCer is galactosyl- and glucosylceramides, GM is monosialogangliosides, LacCer is lactosylceramides, LPC is lysophosphatidylcholine, PC is phosphatidylcholine, PE is phosphatidylethanolamine, PI is phosphatidylinositol, SM is sphingomyelin, S1P is sphingosine-1-phosphate, HETE is hydroxyeicosatetraenoic acid, DHET is dihydroxyeicosatrienoic acid, HODE is hydroxyoctadecadienoic acid, HETrE is hydroxyeicosatrienoic acid, AA is arachidonic acid, HEPE is hydroxy/hydroperoxyeicosapentaenoic acid, EPA is eicosapentaenoic acid, and DHA is docosahexaenoic acid.

The nomenclature X:Y indicates, X number of total carbon atoms in the fatty acid(s) portions of the molecule, and Y the total number of double bonds in the fatty acid portion(s) of the molecule.

The nomenclature A/B indicates, for a molecule of DAG and PC, A and B types of fatty acid moieties attached to the glycerol backbone of the molecule.

The nomenclature (dC/A) indicates, for a molecule of Cer, GlcCer, LacCer and SM, C the type of long-chain base with an amide-linked, A, fatty acid moiety.

As used herein, the term antibody includes monoclonal and polyclonal antibodies, whole antibodies, antibody fragments, and antibody sub-fragments that exhibit specific binding to a said lipid. Thus, suitable antibodies can be whole immunoglobulins of any class, e.g., IgG, IgM, IgA, IgD, IgE, chimeric antibodies or hybrid antibodies with dual or multiple antigen or epitope specificities, or fragments, e.g., F(ab')$_2$, Fab', Fab and the like, including hybrid fragments, and additionally includes any immunoglobulin or any natural, synthetic or genetically engineered protein that acts like an antibody by binding to a specific antigen to form a complex. The term antibody encompasses antigen-binding fragments of antibodies (e.g., single chain antibodies, Fab fragments, F(ab')$_2$, a Fd fragment, a Fv fragment and dAb fragments) as well as complete antibodies. For example, Fab molecules can be expressed and assembled in a genetically transformed host like E. coli. A lambda vector system is available thus to express a population of Fab's with a potential diversity equal to or exceeding that of subject generating the predecessor antibody. See Huse W D, et al., Science 1989, 246:1275-81. Such Fab's are included in the definition of antibody. The ability of a given molecule, including an antibody fragment or sub-fragment, to act like an antibody and specifically bind to a specific antigen can be determined by binding assays known in the art, for example, using the antigen of interest as the binding partner.

Antibodies against lipids in accordance with the present invention may be prepared by methods well known to those skilled in the art. For example, mice may be immunized with a lipid with adjuvant. Splenocytes are harvested as a pool from the mice that were administered 3 immunizations at 2-week intervals with test bleeds performed on alternate weeks for serum antibody titers. Splenocytes are prepared as 3 aliquots that are either used immediately in fusion experiments or stored in liquid nitrogen for use in future fusions.

Fusion experiments are then performed according to the procedure of Stewart & Fuller, *J. Immunol. Methods* 1989, 123:45-53. Supernatants from wells with growing hybrids are screened by enzyme-linked immunosorbent assay (ELISA) for monoclonal antibody (MAb) secretors on 96-well ELISA plates coated with the said lipid. ELISA positive cultures are cloned by limiting dilutions, typically resulting in hybridomas established from single colonies after 2 serial cloning experiments.

EXAMPLES

Example 1

Materials and Methods

For this study the subjects were selected from a cohort of patients presenting clear muscular intolerance phenotypes determined according to strict criteria.

The inclusion criteria for the subjects were the following:
Written informed consent to participate in the study;
Men or women aged 18 years or older;
Documentation of statin-related muscle toxicity manifested by either:
  muscle pain that occurs during statin treatment and stops after withdrawal or reduction in dosage; or
  muscle pain that starts after initiation of statin treatment and persists while still being treated in patients in whom it is considered not possible to stop statin administration; or
  muscle pain that occurs while patient is being treated with a statin and clearly appears to be statin-related in the opinion of his/her physician; or
  patient in whom lipid-lowering regimen is changed from a statin to ezetimibe because of intolerance to statins due to muscle pain or weakness, myopathy or rhabdomyolysis; or
  elevation in plasma CK level more than 1.5 times the upper limit of normal while being treated with a statin, in the absence of other causes to explain the abnormality; or
  presence of myoglobinuria or myoglobinemia while being treated with a statin, in the absence of other causes to explain the abnormality;
  clinical diagnosis of rhabdomyolysis while being treated with a statin, in the absence of other responsible causes.

Exclusion Criteria for the subjects were the following:
patient in whom muscle pain is not clearly associated with the use of a statin in the physician's judgment;
Hypothyroidism that is not controlled with a stable dose of supplement for at least the last 3 months and that occurred during muscle toxicity;
Known hyperthyroidism in the last year and that occurred during muscle toxicity;
History of alcohol or drug abuse in the last year and that occurred during muscle toxicity;
Known renal insufficiency (not secondary to rhabdomyolysis) with serum creatinine level of 200 µmol/L or more at the time of muscle toxicity;
Known severe liver disease with cirrhosis, biliary obstruction, acute or chronic infectious hepatitis at the time of the muscle toxicity;
Known hereditary or acquired muscle disease;
Any medical or psychiatric condition that may make the patient an unsuitable candidate for the study in the physician's opinion.
Participation in any other investigational drug study within 30 days of recruitment.

Inclusion Criteria for the controls were the following:
Written informed consent to participate in the study
Men or women aged 18 years or older;
Known dyslipidemia treated with a stable dose of a statin for at least 3 months;
Absence of current or past statin-related side effects.

Exclusion Criteria for the controls were the following:
Hypothyroidism that is not controlled with a stable dose of supplement for at least the last 3 months unless the absence of muscle toxicity due to statins has been confirmed before condition;
Known hyperthyroidism in the last year unless the absence of muscle toxicity due to statins has been confirmed before condition;
History of alcohol or drug abuse in the last year unless the absence of muscle toxicity due to statins has been confirmed before condition;
Known renal insufficiency with serum creatinine level of 200 µmol/L or more at the time of recruitment unless the absence of muscle toxicity due to statins has been confirmed before condition;
Known severe liver disease with cirrhosis, biliary obstruction, acute or chronic infectious hepatitis at the time of recruitment unless the absence of muscle toxicity due to statins has been confirmed before condition;
Known hereditary or acquired muscle disease;
Any medical or psychiatric condition that may make the patient an unsuitable candidate for the study in the physician's opinion.
Participation in any other investigational drug study within 30 days of recruitment.

TABLE 1

Background characteristics for statin myopathy patients analyzed with Lipidomics

|  | Atorvastatin equivalent dose | Age | CK |
|---|---|---|---|
| Controls (n = 40) | 40.5 | 63 | 94 |
| Cases (n = 40) | 40.5 | 63 | 95 |

Analytical Methods

Mass Spectrometry Driven Lipidomics

Direct infusion coupled to tandem mass spectrometry, i.e. shotgun lipidomics, and two liquid chromatography tandem mass spectrometry (LC-MS/MS) approaches, i.e. ceramide and cerebroside lipidomics and eicosanoid lipidomics, were used to identify statin-induced muscle toxicity by analyzing molecular lipid species in human plasma. The applied methods were optimized especially for quantification of molecular cholesteryl esters (CE), phosphatidylcholines (PC), lysophosphatidylcholines (LPC) and other lysophospholipids (LPL), ether-linked phosphatidylcholines (PC O) and other ether-linked phospholipids (PL O), phosphatidylserines (PS), phosphatidylethanolamines (PE), phosphatidylglycerols (PG), phosphatidylinositols (PI), phosphatidic acids (PA), diacylglycerols (DAG), ceramides (Cer), glucosylceramides (GlcCer), lactosylceramides (LacCer), free fatty acids (FFA) and eicosanoids.

The following materials were used according to the methods. HPLC or LC-MS grade of chloroform, methanol, water, acetonitrile, formic acid, methanol, isopropanol, ammonium acetate, acetic acid, potassium chloride and butylated hydroxytoluene (BHT) were purchased from Sigma-Aldrich (St. Louis, Mo., USA).

HPLC column (Acquity BEH C18, 2.1×50 mm id. 1.7 µm) was purchased from Waters (Milford, Mass., USA). HPLC pre-column (Widepore C18 4×2.0 mm) was purchased from Phenomenex (Torrance, Calif., USA). All labware used for the extraction were resistant to chloroform. Aerosol resistant filter tips (Molecular BioProducts) and Eppendorf 2 ml safe-lock tubes, 96-well twin.tec PCR plates, and Pierce-it-lite thermo-sealing foils were purchased from VWR International (West Chester, Pa., USA). CO-RE Filter Tips and 96-well 2 ml Whatman Uniplates were purchased from Hamilton Robotics (Bonaduz, Switzerland). Synthetic lipid standards were purchased from Avanti Polar Lipids (Alabaster, Ala., USA), Matreya (Pleasant Gap, Pa., USA), and Cayman Chemical (Ann Arbor, Mich., USA).

Lipids were extracted in chloroform:methanol according to the following protocols. Samples were spiked with known amounts of non-endogenous synthetic internal standards for data normalization and endogenous lipid quantification. Post-extract spiked non-endogenous synthetic external standards were used for quality controlling. Stock solutions of standards were prepared by dissolving appropriately weighed amounts of each standard in chloroform:methanol (2:1, v/v) to achieve a final concentration of 500 µM. An internal standard mixture containing each of the standard stock was created and used in lipid extraction.

5 µl of plasma was used for shotgun lipidomics and 10 µl of plasma for ceramide and cerebroside lipidomics Lipid extractions were carried out in automated fashion using a Hamilton MICROLAB STAR system (Hamilton Robotics, Switzerland). Well-mixed samples were aliquoted into a 96-well 2 ml Whatman Uniplate containing ice-cold methanol and 0.1% BHT. The samples were mixed thoroughly after each step in the extraction protocol. The extraction proceeded at room temperature by adding an appropriate volume of internal standard mixture and chloroform and methanol. In shotgun and ceramide and cerebroside lipidomics, the organic phase separation was facilitated by adding 20 mM acetic acid and centrifuging the plate for 5 min at 500×g. The organic phase was transferred into a new 96-well 2 ml Whatman Uniplate. The remaining water-containing phase was washed by adding appropriate volume of chloroform followed by centrifugation. The two organic phases were pooled and evaporated under $N_2$ until dryness. The lipid extracts were then re-dissolved in chloroform:methanol (1:2, v/v) including the addition of the synthetic external standard. The extracts were stored in 2 ml safe-lock Eppendorf tubes at −20° C. prior to MS analysis. Required volumes of lipid extracts were aliquoted into an Eppendorf 96-well twin.tec PCR plate and the plate was heat-sealed with aluminum foil to avoid evaporation.

In shotgun lipidomics, lipid extracts were analyzed on a hybrid triple quadrupole/linear ion trap mass spectrometer (QTRAP 5500, AB Sciex) equipped with a robotic nanoflow ion source (NanoMate HD, Advion Biosciences). The instruments were operated in positive and negative ion modes. In positive ion the spray voltage was set to 1.0 to 1.4 kV and in negative ion mode to −1.0 to −1.4 kV. A gas pressure of 0.3-0.8 psi was used and the interface heater was set at 60° C. The collision energy (CE) and declustering potential (DP) was optimized for each lipid class using synthetic standards. The mass spectrometer was operated in unit resolution mode using a scan speed of 200 Da/s. Molecular lipids were analyzed in both positive and negative ion modes using multiple precursor ion scanning (MPIS) and neutral loss scanning (NLS) as described by Stahlman and colleagues (Stahlman M, et al: *High-throughput shotgun lipidomics by quadrupole time-of-flight mass spectrometry. J Chromatogr B Analyt Technol Biomed Life Sci* 2009).

In ceramide and cerebroside lipidomics, the high performance liquid chromatography (HPLC) analyses were conducted in the following way. Chromatographic apparatus consisted of a CTC HTC PAL autosampler (CTC Analytics AG, Switzerland), a Rheos Allegro UHPLC pump (Flux Instruments AG, Switzerland), an external column heater set to 60° C. for ceramide and cerebroside lipidomics and the Acquity BEH C18 column with an in-line pre-column. The extracted samples, 10 µl of each, were injected into the pre-column followed by the analytical column and delivered to the mass spectrometer at a flow rate of 500 µ/min In ceramide and cerebroside lipidomics, A gradient was used for lipid analyte separation with solvent A comprising 10 mM ammonium acetate in HPLC grade water containing 0.1% formic acid and solvent B of 10 mM ammonium acetate in acetonitrile:isopropanol (4:3, v/v) containing 0.1% formic acid. The gradient was constructed in the following way: 0 min-65% B; 2 min-65% B; 2.5 min-75% B; 17.5 min-100% B; 22.5 min-100% B; 22.6 min-65% B; 25 min-65% B.

The lipid extracts were analyzed by HPLC-MS/MS. The MS analysis was performed on a hybrid triple quadrupole/linear ion trap mass spectrometer equipped with the Turbo V™ Ion Source (4000 QTRAP, AB Sciex). The instrument was operating in positive ion mode. The ion source voltage was set to 5500V for ceramide and cerebroside lipidomics and to −4500V for ganglioside lipidomics, and source temperature at 400° C. The collision energy (CE) and declustering potential (DP) was optimized for each lipid class using synthetic standards. A 20 sec dwell time was applied for each scan. Multiple reaction monitoring (MRM) scan mode was applied and based on the description by Sullards and colleagues (Sullards M C, et al: *Structure-specific, quantitative methods for analysis of sphingolipids by liquid chromatography-tandem mass spectrometry: "inside-out" sphingolipidomics. Methods Enzymol* 2007).

Eicosanoids were extracted using solid phase extraction (SPE). 150 µl plasma was extracted with 10% methanol containing 0.1% of butylated hydroxytoluene (BHT). Samples were spiked with known amounts of non-endogenous synthetic internal standards for data normalization and endogenous lipid quantification. An internal standard mixture containing each of the standard stock was created and used in lipid extraction. Strata-X 33 um SPE cartridges were conditioned with HPLC grade methanol followed by a conditioning step with ultra pure water (UPW). Samples were loaded onto the SPE followed by a wash step using 35% methanol. Eicosanoids were eluted with acetonitrile and the sample elutes were dried down under nitrogen. The final sample extracts were reconstituted in methanol and directly analyzed by mass spectrometry.

In the analysis for Eicosanoids, high performance liquid chromatography (HPLC) analyses were conducted in the following way: Chromatographic apparatus consisted of a CTC HTC PAL autosampler (CTC Analytics AG, Switzerland), a Rheos Allegro UHPLC pump (Flux Instruments AG, Switzerland), an external column heater set to 45° C. and switching valve (Valco Instruments Co. Inc. and VICI AG, Huston, USA). Separation was carried out using a Phenomenex Jupiter, 250×2.0 mm id. 5 µm HPLC column (Phenomenex, Inc, Torrance, Calif.). The extracted samples, 10 µl of each, were injected into the analytical column and delivered to the mass spectrometer at a flow rate of 300 µl/min A gradient was used for lipid analyte separation with solvent A comprising of acetonitrile:water (63:37 (v/v)) containing 0.1% formic acid and solvent B of acetonitrile: isopropanol (50:50 (v/v)). The gradient was constructed in the following way: 0 min-0% B; 6 min -20% B; 6.50 min-55% B; 10.0 min-55% B; 12.0 min-100% B; 14.0 min-100% B; 14.50 min-0% B; 18.0 min-0% B.

The lipid extracts were analyzed by HPLC-MS/MS. The MS analysis was performed on a hybrid triple quadrupole/linear ion trap mass spectrometer equipped with the Turbo V™ Ion Source (4000 QTRAP, AB Sciex). The instrument was operating in negative ion mode and the ion source voltage was set to −4500V. The collision energy (CE) and declustering potential (DP) was optimized for each lipid class using synthetic standards where available. Multiple reaction monitoring (MRM) scan mode was applied and based on the description by Deems and colleagues (Deems, R., et al: *Detection and quantitation of eicosanoids via high performance liquid chromatography-electrospray ionization-mass spectrometry. Methods Enzymol* 2007).

The data processing was done in the following way: Initially the retention time (in LC mode) and identification of each peak was done using endogenous standards and by Information Dependent Acquisition (IDA) experiments where applicable. The raw data were processed according to peak detected and retention time (in LC mode) in automated fashion. A stringent cutoff was applied for separating background noise from actual lipid peaks. Each sample was controlled and only accepted when fulfilling the stringent acceptance criteria. Peak area counts (cps) of detected peaks were converted into a list of corresponding lipid names. Lipids were normalized to their respective internal standard and sample volume to retrieve their concentrations.

The ratio of synthetic Internal Standards (IS) to corresponding post-extract spiked External Standards (ES), and MS analysis of extracted matrix and solvents served as quality controls (QC) of the analysis. In addition, extracted reference plasma samples were analyzed for monitoring the instruments' performance, i.e., the intra- and inter-assay variation.

A calibration line using synthetic or isolated standards was obtained prior to sample analysis. Synthetic standards were chosen based on application and had similar properties to the endogenous lipids or analyte(s) of interest. The calibration line consisted of a minimum of five standards points covering the expected quantification range. The calibration line was used to determine the dynamic quantification range for each lipid class monitored, e.g., the linear quantification limits. As the internal standards used behave in the same way as endogenous lipids they were used for quantifying endogenous lipid species. The calibration lines were based on the same internal standards that were used for quantification of the endogenous lipids.

For each platform, a stringent cutoff was applied for separating background noise from actual lipid peaks. Each sample was controlled and only accepted when fulfilling the acceptance criteria. Masses and counts of detected peaks were converted into a list of corresponding lipid names. Lipids were normalized to their respective internal standard and sample volume to retrieve their concentrations.

Statistical Analyses

Percentage changes in lipid concentrations between control and case groups were calculated as follows:

100*(AVG[C] in case group−AVG[C] in control group)/AVG[C] in control group.

Statistical significance was assigned based on two independent samples t-test and Mann-Whitney U-test p-values.

In addition, ROC curves were used for finding lipid molecules and concentration cutoffs that separate the best cases from controls. Sensitivity is calculated as a number of correctly identified cases divided by the total number of cases. Specificity is calculated as a number of correctly identified controls divided by the total number of controls. Sensitivity and specificity was calculated for each lipid concentration, lipid to lipid ratio and ratio of lipid to clinical concentrations. Significant biomarkers were defined as those molecules or ratios that have a t-test based p-value of 0.05 or Sensitivity>=60% and Specificity=>40%

Figure 2:
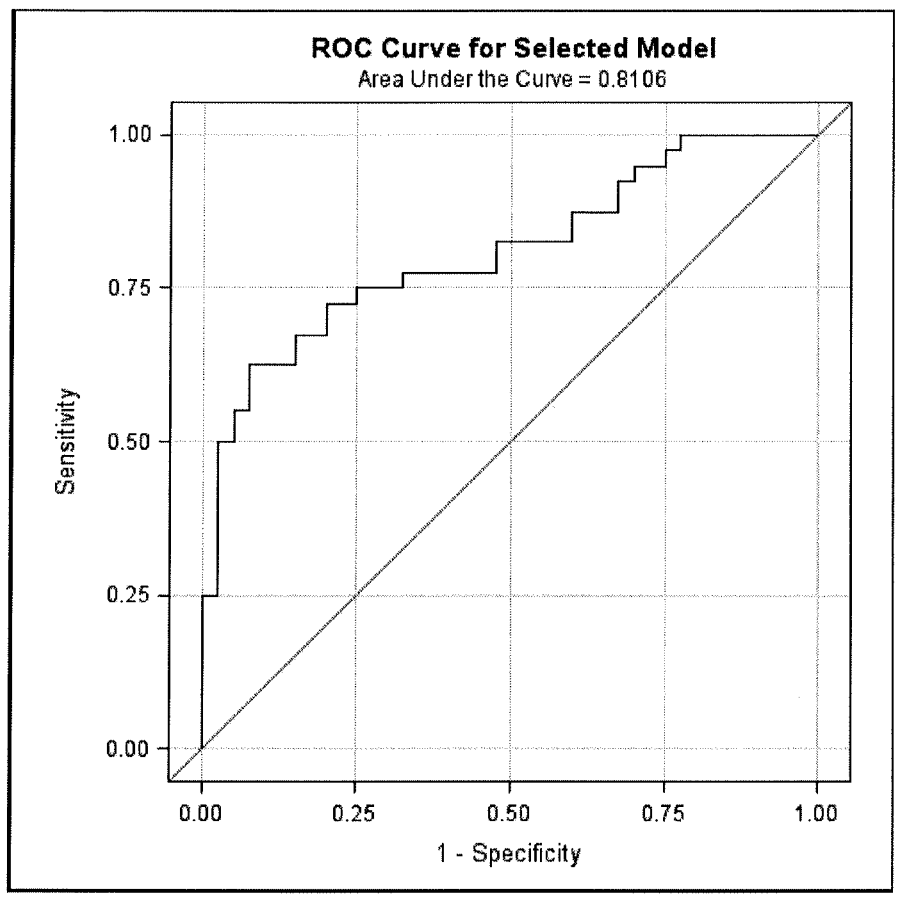
FIG. 2. ROC curve of three significant lipids, 8_9-DHET and 15-HETE and 15-HETrE, separating the cases and controls.
Figure 3:
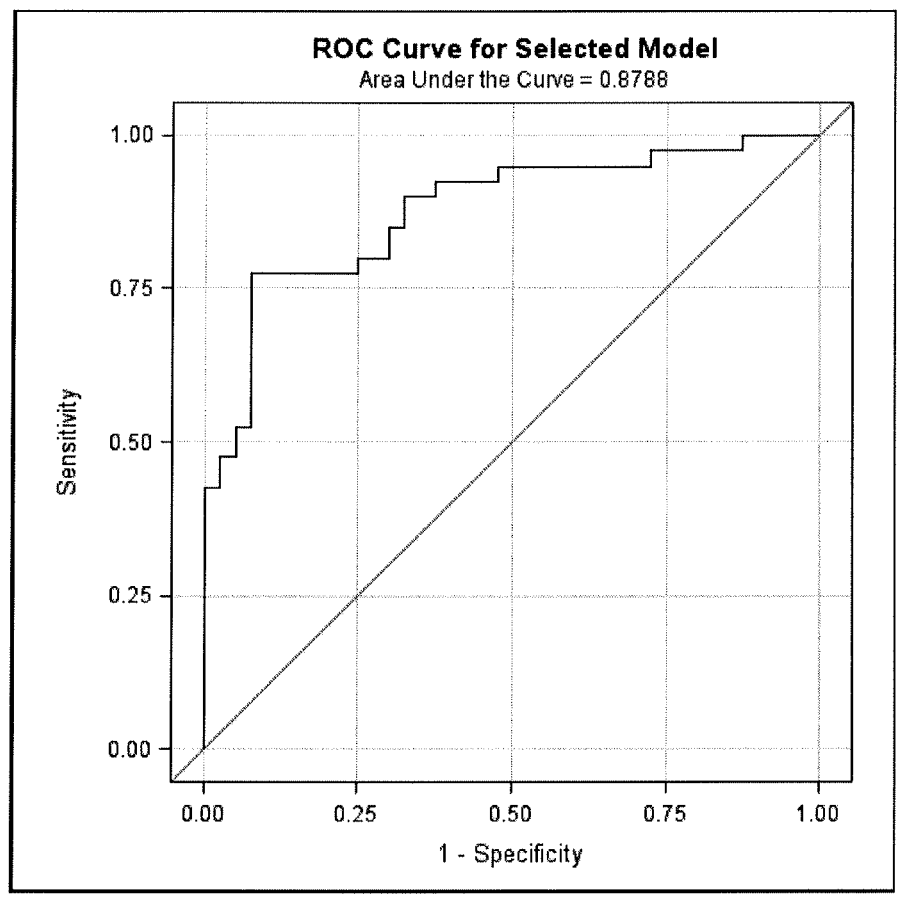
FIG. 3. ROC curve on combination of 15-HETE, 15-HETrE, Cer(d18:1/18:0), Cer(d18:1/22:0), 9-HODE and 5-HETE.

Furthermore, to demonstrate improved diagnostic potential, an example of logistic regression model using lipid combinations is demonstrated in Table 7. Logistic models were fitted in order to find different combinations of lipids that could separate cases and controls from each other. First, all the lipids were set as possible explanatory variables and model was selected using stepwise method with entry significance level of 0.1 and stay significance level of 0.05. Two significant lipids were found, 8_9-DHET and 15-HETE. With these two lipids in the model, AUC value is 0.8056 (FIG. 1). With increased entry and stay values, one more lipid, 15-HETrE, is included in the model, giving the AUC-value of 0.8106 (FIG. 2). Same model was fitted but with increased entry and stay significance values. This means, that the used criteria for selecting the lipids to the model are not as strict as they were in the previous model. With these looser criteria, six lipids were selected to the model, 15-HETE, 15-HETrE, Cer(d18:1/18:0), Cer(d18:1/22:0), 9-HODE and 5-HETE. With these lipids, AUC value is 0.8788 (FIG. 3).

Results

In the study sample group the creatine kinase levels were practically identical in controls and cases, therefore this traditionally used enzyme marker was not predictive or diagnostic for statin-induced myopathy.

On the other hand, lipidomic biomarkers appeared as significant biomarkers of the statin-induced myopathy. As a total 290 molecular lipids were quantified in this study as described above. Out of those 27 molecular lipids were significant biomarkers based on set statistical criteria. The significant biomarker candidates based on molecular lipid concentrations are presented in Table 2. The diagnostic value as lipidomic biomarkers was increased when their levels were expressed as distinct lipid-lipid ratios. The biomarker candidates based on ratios are listed in the Tables 3 and 4.

The preferred embodiments selected among the identified biomarker candidates are listed in Tables 5 and 6.

TABLE 2

Significant biomarkers based on individual lipid or fatty acid measurement. Species names, p-values, percentage change, auc-values; and specificity and sensitivity are presented.

| Lipid/Fatty acid name | p-value | Percentage change | AUC | Sensitivity | Specificity |
|---|---|---|---|---|---|
| Increased | | | | | |
| 12-HETE | 0.00083788 | 317.4 | 0.71 | 68 | 73 |
| 15-HETE | 0.00044400 | 164.8 | 0.68 | 73 | 60 |
| 13-HODE | 0.00233970 | 78.3 | 0.67 | 68 | 50 |
| PE P-18:0/20:4 (PE O-18:1/20:4) | 0.04733164 | 63.9 | 0.73 | 67 | 81 |
| LacCer(d18:1/22:0) | 0.00066200 | 48.9 | 0.68 | 60 | 65 |
| LacCer(d18:1/20:0) | 0.00339138 | 41.1 | 0.66 | 60 | 58 |
| PE 18:0/20:4 | 0.02048354 | 36.6 | 0.68 | 76 | 62 |
| Cer(d18:1/18:0) | 0.00482621 | 33.3 | 0.68 | 68 | 65 |
| LacCer(d18:1/24:0) | 0.00612076 | 33.3 | 0.64 | 60 | 51 |
| Cer(d18:1/20:0) | 0.00444907 | 30.3 | 0.68 | 68 | 63 |
| PC16:0/20:3 | 0.04196334 | 26.0 | 0.62 | 62 | 51 |
| AA | 0.01455690 | 22.7 | 0.65 | 68 | 68 |
| Cer(d18:1/24:1) | 0.04947448 | 20.8 | 0.64 | 63 | 68 |
| Cer(d18:1/26:1) | 0.01665485 | 19.8 | 0.65 | 83 | 60 |
| Glc/GalCer(d18:1/24:1) | 0.03833543 | 19.0 | 0.63 | 60 | 63 |
| Cer(d18:1/22:0) | 0.10376969 | 16.6 | 0.62 | 60 | 63 |
| Glc/GalCer(d18:1/18:0) | 0.02168179 | 16.3 | 0.65 | 63 | 63 |
| Cer(d18:1/16:0) | 0.02664162 | 15.2 | 0.63 | 60 | 60 |
| LacCer(d18:1/24:1) | 0.03043011 | 15.0 | 0.64 | 68 | 65 |
| SM (d18:1/14:0) (d18:1/13:1-OH) | 0.11114277 | 13.9 | 0.62 | 79 | 63 |
| LacCer(d18:1/16:0) | 0.01665073 | 12.6 | 0.68 | 70 | 60 |
| CE 18:3 | 0.30263261 | 8.7 | 0.58 | 63 | 60 |
| PC 16:0/20:4 | 0.48442590 | 6.4 | 0.56 | 63 | 62 |
| Decreased | | | | | |
| 11_12-DHET | 0.09660998 | −15.9 | 0.63 | 63 | 50 |
| 14_15-DHET | 0.00651153 | −19.4 | 0.69 | 73 | 60 |
| 5-HETrE | 0.02776571 | −21.4 | 0.65 | 62 | 60 |
| 5-HETE | 0.00987273 | −36.1 | 0.70 | 78 | 63 |
| 8_9-DHET | 0.00032550 | −38.2 | 0.72 | 63 | 65 |

TABLE 3

Measurements used in calculating ratios separating the study groups. Any combination of at least two of these measurements are used in a ratio.

| Measurement class | Measurement name |
|---|---|
| Creatine kinase | CK |
| CE | CE 14:0 |
| | CE 16:0 |
| | CE 16:1 |
| | CE 18:1 |
| | CE 18:2 |
| | CE 18:3 |
| | CE 20:3 |
| | CE 20:4 |
| | CE 20:5 |
| | CE 22:6 |
| Cer | Cer(d18:1/16:0) |
| | Cer(d18:1/18:0) |
| | Cer(d18:1/20:0) |
| | Cer(d18:1/22:0) |
| | Cer(d18:1/24:0) |
| | Cer(d18:1/24:1) |
| | Cer(d18:1/26:0) |
| | Cer(d18:1/26:1) |
| Eico | 5-HEPE |
| | 5-HETE |
| | 5-HETrE |
| | 8_9-DHET |
| | 9-HODE |
| | 11-HETE |
| | 11_12-DHET |
| | 12-HETE |
| | 13-HODE |
| | 14_15-DHET |
| | 15-HETE |
| | 15-HETrE |
| Gb3 | Gb3(d18:1/22:0) |
| | Gb3(d18:1/24:0) |
| | Gb3(d18:1/24:1) |
| Glc/GalCer | Glc/GalCer(d18:1/16:0) |
| | Glc/GalCer(d18:1/18:0) |
| | Glc/GalCer(d18:1/20:0) |
| | Glc/GalCer(d18:1/22:0) |
| | Glc/GalCer(d18:1/24:0) |
| | Glc/GalCer(d18:1/24:1) |
| LacCer | LacCer(d18:1/16:0) |
| | LacCer(d18:1/22:0) |
| | LacCer(d18:1/24:0) |
| | LacCer(d18:1/24:1) |
| LPC | LPC 16:0 |
| | LPC 18:1 |
| PC | PC 16:0/18:1 |
| | PC 16:0/18:2 |
| | PC 16:0/20:3 |
| | PC 16:0/20:4 |
| | PC 18:0/18:2 |
| | PC 18:0/20:4 |
| PE | PE 18:0/20:4 |
| PE P | PE P-18:0/20:4 (PE O-18:1/20:4) |

TABLE 3-continued

Measurements used in calculating ratios separating the study groups. Any combination of at least two of these measurements are used in a ratio.

| Measurement class | Measurement name |
|---|---|
| PI | PI 18:0/20:4 |
| SM | SM (d18:1/14:0) (d18:1/13:1-OH) |
|  | SM (d18:1/16:0) (d18:1/15:1-OH) |
|  | SM (d18:1/16:1) (d18:1/15:2-OH) |
|  | SM (d18:1/18:0) |
|  | SM (d18:1/23:0) (d18:1/22:1-OH) |
|  | SM (d18:1/24:0) (d18:1/23:1-OH) |
|  | SM (d18:1/24:1) (d18:1/23:2-OH) |
| FA | AA |
|  | DHA |
|  | EPA |

TABLE 4

Significant biomarkers based on ratios. The significant biomarkers are selected based on p-value, percentage change, AUC-value, sensitivity and specificity.

| Ratio | p-value | Percentage change | AUC | Sensitivity | Specificity |
|---|---|---|---|---|---|
| Increased |  |  |  |  |  |
| 12-HETE/5-HETrE | 0.00019432 | 591.8 | 0.73 | 67 | 78 |
| 12-HETE/8_9-DHET | 0.00011975 | 572.5 | 0.76 | 70 | 60 |
| 12-HETE/5-HETE | 0.00004403 | 564.6 | 0.74 | 68 | 78 |
| 12-HETE/14_15-DHET | 0.00039144 | 431.7 | 0.74 | 73 | 63 |
| 12-HETE/CE 20:4 | 0.00218904 | 402.1 | 0.70 | 68 | 78 |
| 12-HETE/15-HETrE | 0.00000305 | 387.4 | 0.76 | 73 | 60 |
| 12-HETE/LPC 16:0 | 0.00056978 | 383.1 | 0.70 | 68 | 77 |
| 15-HETE/8_9-DHET | 0.00020387 | 381.8 | 0.77 | 73 | 63 |
| 12-HETE/5-HEPE | 0.00097305 | 378.5 | 0.71 | 74 | 60 |
| 12-HETE/PC 18:0/18:2 | 0.00154220 | 347.8 | 0.70 | 68 | 72 |
| 12-HETE/CK | 0.00014198 | 347.1 | 0.71 | 68 | 83 |
| 15-HETE/5-HETE | 0.00013546 | 335.3 | 0.73 | 73 | 63 |
| 12-HETE/CE 18:3 | 0.00136124 | 270.1 | 0.69 | 68 | 75 |
| 13-HODE/8_9-DHET | 0.00037669 | 199.4 | 0.77 | 80 | 68 |
| 15-HETE/15-HETrE | 0.00000785 | 160.8 | 0.75 | 73 | 70 |
| Decreased |  |  |  |  |  |
| 11_12-DHET/CE 18:2 | 0.00000000 | −18.8 | 0.66 | 73 | 65 |
| 14_15-DHET/CE 18:2 | 0.00000000 | −24.0 | 0.70 | 75 | 60 |
| 11_12-DHET/LacCer(d18:1/24:0) | 0.04901712 | −24.8 | 0.70 | 65 | 74 |
| 11_12-DHET/Cer(d18:1/16:0) | 0.01709201 | −25.7 | 0.70 | 65 | 75 |
| 5-HETE/CE 20:4 | 0.00000000 | −27.5 | 0.69 | 73 | 63 |
| 14_15-DHET/LacCer(d18:1/22:0) | 0.00663328 | −31.1 | 0.73 | 70 | 73 |
| 14_15-DHET/Glc/GalCer(d18:1/18:0) | 0.00025290 | −32.3 | 0.75 | 83 | 60 |
| 15-HETrE/LacCer(d18:1/22:0) | 0.00818539 | −32.6 | 0.66 | 63 | 75 |
| 11_12-DHET/Cer(d18:1/20:0) | 0.00299230 | −33.8 | 0.73 | 68 | 73 |
| 5-HETE/CE 18:2 | 0.00000000 | −36.5 | 0.70 | 75 | 63 |
| 5-HETE/CE 18:1 | 0.00000000 | −37.1 | 0.72 | 75 | 60 |
| 8_9-DHET/CE 18:2 | 0.00000000 | −38.9 | 0.74 | 73 | 63 |
| 8_9-DHET/CE 18:1 | 0.00000000 | −40.4 | 0.75 | 83 | 63 |
| 8_9-DHET/CE 22:6 | 0.00355177 | −41.0 | 0.73 | 83 | 62 |
| 14_15-DHET/Cer(d18:1/18:0) | 0.00060519 | −41.1 | 0.76 | 80 | 60 |
| 5-HETE/LacCer(d18:1/24:1) | 0.00102757 | −41.6 | 0.72 | 73 | 73 |
| 8_9-DHET/CE 16:0 | 0.00094633 | −41.6 | 0.74 | 83 | 63 |
| 5-HETE/Glc/GalCer(d18:1/18:0) | 0.00081471 | −42.5 | 0.76 | 78 | 65 |
| 8_9-DHET/Cer(d18:1/26:0) | 0.00060560 | −42.6 | 0.76 | 80 | 65 |
| 8_9-DHET/LacCer(d18:1/16:0) | 0.00020074 | −42.7 | 0.74 | 83 | 60 |
| 5-HETE/9-HODE | 0.01286018 | −44.6 | 0.72 | 83 | 60 |
| 8_9-DHET/Cer(d18:1/16:0) | 0.00009653 | −45.1 | 0.76 | 83 | 60 |
| 8_9-DHET/Cer(d18:1/26:1) | 0.00032914 | −46.3 | 0.77 | 85 | 60 |
| 8_9-DHET/Glc/GalCer(d18:1/18:0) | 0.00002468 | −46.7 | 0.76 | 88 | 60 |
| 11_12-DHET/12-HETE | 0.04511422 | −48.6 | 0.74 | 70 | 65 |
| 8_9-DHET/9-HODE | 0.00040272 | −49.1 | 0.72 | 70 | 60 |
| 5-HETE/Cer(d18:1/18:0) | 0.00004199 | −49.4 | 0.77 | 83 | 60 |
| 8_9-DHET/AA | 0.00023962 | −49.9 | 0.77 | 75 | 60 |
| 5-HETE/PC 16:0/20:3 | 0.00216323 | −50.5 | 0.72 | 69 | 69 |
| 8_9-DHET/Cer(d18:1/24:1) | 0.00019510 | −50.8 | 0.74 | 80 | 60 |
| 8_9-DHET/CE 16:1 | 0.00051753 | −51.4 | 0.73 | 75 | 60 |
| 11-HETE/12-HETE | 0.00076920 | −52.2 | 0.76 | 73 | 60 |
| 8_9-DHET/Cer(d18:1/20:0) | 0.00002608 | −52.4 | 0.77 | 78 | 60 |
| 8_9-DHET/PC 16:0/20:3 | 0.00036513 | −52.6 | 0.73 | 69 | 72 |
| 8_9-DHET/Cer(d18:1/18:0) | 0.00003122 | −53.9 | 0.77 | 85 | 60 |

TABLE 5

Preferred embodiments of biomarkers based on one lipid or fatty acid measurement

| Lipid name | p-value | Percentage change | AUC | Sensitivity | Specificity |
|---|---|---|---|---|---|
| *Increased* | | | | | |
| 12-HETE | 0.00083788 | 317.4 | 0.71 | 68 | 73 |
| 15-HETE | 0.00044400 | 164.8 | 0.68 | 73 | 60 |
| PE P-18:0/20:4 (PE O-18:1/20:4) | 0.04733164 | 63.9 | 0.73 | 67 | 81 |
| LacCer(d18:1/22:0) | 0.00066200 | 48.9 | 0.68 | 60 | 65 |
| Cer(d18:1/18:0) | 0.00482621 | 33.3 | 0.68 | 68 | 65 |
| *Decreased* | | | | | |
| 5-HETE | 0.00987273 | −36.1 | 0.70 | 78 | 63 |
| 8_9-DHET | 0.00032550 | −38.2 | 0.72 | 63 | 65 |

TABLE 6

Preferred embodiments of biomarkers based on a measurement ratio.

| Measurement ratios | p-value | Percentage change | AUC | Sensitivity | Specificity |
|---|---|---|---|---|---|
| *Increased* | | | | | |
| 12-HETE/5-HETrE | 0.00019432 | 591.8 | 0.73 | 67 | 78 |
| 12-HETE/5-HETE | 0.00004403 | 564.6 | 0.74 | 68 | 78 |
| 12-HETE/CE 20:4 | 0.00218904 | 402.1 | 0.70 | 68 | 78 |
| 12-HETE/15-HETrE | 0.00000305 | 387.4 | 0.76 | 73 | 60 |
| 12-HETE/LPC 16:0 | 0.00056978 | 383.1 | 0.70 | 68 | 77 |
| 15-HETE/8_9-DHET | 0.00020387 | 381.8 | 0.77 | 73 | 63 |
| 12-HETE/CK | 0.00014198 | 347.1 | 0.71 | 68 | 83 |
| 13-HODE/8_9-DHET | 0.00037669 | 199.4 | 0.77 | 80 | 68 |
| 15-HETE/15-HETrE | 0.00000785 | 160.8 | 0.75 | 73 | 70 |
| *Decreased* | | | | | |
| 11_12-DHET/Cer(d18:1/16:0) | 0.01709181 | −25.7 | 0.70 | 65 | 75 |
| 5-HETE/CE 18:2 | 0.00000000 | −36.5 | 0.70 | 75 | 63 |
| 8_9-DHET/CE 18:1 | 0.00000000 | −40.4 | 0.75 | 83 | 63 |
| 8_9-DHET/LacCer(d18:1/16:0) | 0.00020074 | −42.7 | 0.74 | 83 | 60 |
| 5-HETE/9-HODE | 0.01286018 | −44.6 | 0.72 | 83 | 60 |
| 8_9-DHET/Glc/GalCer(d18:1/18:0) | 0.00002468 | −46.7 | 0.76 | 88 | 60 |
| 5-HETE/Cer(d18:1/18:0) | 0.00004199 | −49.4 | 0.77 | 83 | 60 |
| 8_9-DHET/Cer(d18:1/24:1) | 0.00019510 | −50.8 | 0.74 | 80 | 60 |
| 11-HETE/12-HETE | 0.00076920 | −52.2 | 0.76 | 73 | 60 |
| 8_9-DHET/Cer(d18:1/18:0) | 0.00003122 | −53.9 | 0.77 | 85 | 60 |

TABLE 7

Example of lipid combinations generated with logistic modelling. The lipid combinations produce higher AUC values compared to the single measurements and thus improves diagnostic potential. The direction of change of the individual lipid marker in cases compared to the controls is indicated in the table.
Best predictive models

| Number of species | AUC | Lipid markers | Direction of change |
|---|---|---|---|
| 6 | 0.8788 | 15-HETE, Cer(d18:1/18:0), Cer(d18:1/22:0), | Increased |
| | | 15-HETrE, 9-HODE and 5-HETE | Decreased |
| 3 | 0.8106 | 15-HETE, | Increased |
| | | 8_9-DHET, and 15-HETrE | Decreased |
| 2 | 0.8056 | 15-HETE and | Increased |
| | | 8_9-DHET | Decreased |

The data in FIGS. 1 to 3 show that three different combinations of lipids were predictive biomarkers for indicating statin-induced myopathy: (i) 15-HETE, 15-HETrE, Cer(d18:1/18:0), Cer(d18:1/22:0), 9-HODE and 5-HETE; (ii) 8_9-DHET, 15-HETE and 15-HETrE; and (iii) 8_9-DHET and 15-HETE (see Table 7).

In summary, this study provides novel lipid markers of statin-induced muscle toxicity. Since the creatine kinase levels in the study sample group were practically identical in controls and cases (Table 1), the lipidomic biomarkers were more specific and sensitive markers of the statin-induced muscle toxicity.

The invention claimed is:

1. A method of detecting a lipid in a subject, comprising:
(a) assaying a sample from said subject to determine the concentration of one or more lipids wherein the one or more lipids is selected from: 12-HETE, 15-HETE, 13-HODE, PE P-18:0/20:4, PE O-18:1/20:4, LacCer (d18:1/22:0), LacCer(d18:1/20:0), PE 18:0/20:4, Cer (d18:1/18:0), LacCer(d18:1/24:0), Cer(d18:1/20:0), PC16:0/20:3, AA, Cer(d18:1/24:1), Cer(d18:1/26:1), Glc/GalCer(d18:1/24:1), Cer(d18:1/22:0), Glc/GalCer (d18:1/18:0), Cer(d18:1/16:0), LacCer(d18:1/24:1), SM(d18:1/14:0)(d18:1/13:1-OH), LacCer(d18:1/16:0), CE 18:3, PC 16:0/20:4, 11_12-DHET, 14_15-DHET, 5-HETrE, 5-HETE and 8_9-DHET; or
(b) assaying a sample from said subject to determine the concentration of one or more lipid-lipid concentration ratios, wherein the one or more lipid-lipid concentration ratios is selected from: 12-HETE/5-HETrE, 12-HETE/8_9-DHET, 12-HETE/5-HETE, 12-HETE/ 14_15-DHET, 12-HETE/CE 20:4, 12-HETE/15-HETrE, 12-HETE/LPC 16:0, 15-HETE/8_9-DHET, 12-HETE/5-HEPE, 12-HETE/PC 18:0/18:2, 12-HETE/ CK, 15-HETE/5-HETE, 12-HETE/CE 18:3, 13-HODE/8_9-DHET, 15-HETE/15-HETrE, 11_12-DHET/CE 18:2, 14_15-DHET/CE 18:2, 11_12-DHET/ LacCer(d18:1/24:0), 11_12-DHET/Cer(d18:1/16:0), 5-HETE/CE 20:4, 14_15-DHET/LacCer(d18:1/22:0), 14_15-DHET/Glc/GalCer(d18:1/18:0), 15-HETrE/ LacCer(d18:1/22:0), 11_12-DHET/Cer(d18:1/20:0), 5-HETE/CE 18:2, 5-HETE/CE 18:1, 8_9-DHET/CE 18:2, 8_9-DHET/CE 18:1, 8_9-DHET/CE 22:6, 14_15-DHET/Cer(d18:1/18:0), 5-HETE/LacCer(d18:1/24:1), 8_9-DHET/CE 16:0, 5-HETE/Glc/GalCer(d18:1/18:0), 8_9-DHET/Cer(d18:1/26:0), 8_9-DHET/LacCer(d18:1/16:0), 5-HETE/9-HODE, 8_9-DHET/Cer(d18:1/16:0), 8_9-DHET/Cer(d18:1/26:1), 8_9-DHET/Glc/GalCer(d18:1/18:0), 11_12-DHET/12-HETE, 8_9-DHET/9-HODE, 5-HETE/Cer(d18:1/18:0), 8_9-DHET/AA, 5-HETE/PC 16:0/20:3, 8_9-DHET/Cer(d18:1/24:1), 8_9-DHET/CE 16:1, 11-HETE/12-HETE, 8_9-DHET/Cer(d18:1/20:0), 8_9-DHET/PC 16:0/20:3 and 8_9-DHET/Cer(d18:1/18:0), and wherein the subject is at an increased risk of developing statin-induced muscle toxicity or the subject is suffering from statin-induced muscle toxicity and/or one or more complications of statin-induced muscle toxicity, wherein the one or more complications are selected from myalgia, myositis, myopathy or rhabdomyolysis.

2. A method for determining whether to adjust treatment of a subject undergoing treatment with a statin and/or a lipid lowering drug; comprising:
(a) assaying a sample from said subject to determine the concentration of one or more lipids, wherein an increased or decreased concentration in said sample, when compared to a control, is indicative of said treatment requiring adjustment, wherein the one or more lipids whose increase in concentration is compared to the control is selected from: 12-HETE, 15-HETE, 13-HODE, PE P-18:0/20:4, PE O-18:1/20:4, LacCer(d18:1/22:0), LacCer(d18:1/20:0), PE 18:0/20:4, Cer(d18:1/18:0), LacCer(d18:1/24:0), LacCer(d18:1/20:0), PC16:0/20:3, AA, Cer(d18:1/24:1), Cer(d18:1/26:1), Glc/GalCer(d18:1/24:1), Cer(d18:1/22:0), Glc/GalCer(d18:1/18:0), Cer(d18:1/16:0), LacCer(d18:1/24:1), SM (d18:1/14:0) (d18:1/13:1-OH), LacCer(d18:1/16:0), CE 18:3, and PC 16:0/20:4,
and wherein the one or more lipids whose decrease in concentration is compared to the control is selected from 11_12-DHET, 14_15-DHET, 5-HETrE, 5-HETE and 8_9-DHET; or
(b) assaying a sample from said subject to determine the concentration of one or more lipid-lipid concentration ratios, wherein an increased or decreased concentration in said sample, when compared to a control, is indicative of said treatment requiring adjustment, wherein the one or more lipid-lipid concentration ratios whose increase in concentration is compared to the control is selected from: 12-HETE/5-HETrE, 12-HETE/8_9-DHET, 12-HETE/5-HETE, 12-HETE/14_15-DHET, 12-HETE/CE 20:4, 12-HETE/15-HETrE, 12-HETE/LPC 16:0, 15-HETE/8_9-DHET, 12-HETE/5-HEPE, 12-HETE/PC 18:0/18:2, 12-HETE/CK, 15-HETE/5-HETE, 12-HETE/CE 18:3, 13-HODE/8_9-DHET and 15-HETE/15-HETrE,
and wherein the one or more lipid-lipid concentration ratios whose decrease in concentration is compared to the control is selected from: 11_12-DHET/CE 18:2, 14_15-DHET/CE 18:2, 11_12-DHET/LacCer(d18:1/24:0), 11_12-DHET/Cer(d18:1/16:0), 5-HETE/CE 20:4, 14_15-DHET/LacCer(d18:1/22:0), 14_15-DHET/Glc/GalCer(d18:1/18:0), 15-HETrE/LacCer(d18:1/22:0), 11_12-DHET/Cer(d18:1/20:0), 5-HETE/CE 18:2, 5-HETE/CE 18:1, 8_9-DHET/CE 18:2, 8_9-DHET/CE 18:1, 8_9-DHET/CE 22:6, 14_15-DHET/Cer(d18:1/18:0), 5-HETE/LacCer(d18:1/24:1), 8_9-DHET/CE 16:0, 5-HETE/Glc/GalCer(d18:1/18:0), 8_9-DHET/Cer(d18:1/26:0), 8_9-DHET/LacCer(d18:1/16:0), 5-HETE/9-HODE, 8_9-DHET/Cer(d18:1/16:0), 8_9-DHET/Cer(d18:1/26:1), 8_9-DHET/Glc/GalCer(d18:1/18:0), 11_12-DHET/12-HETE, 8_9-DHET/9-HODE, 5-HETE/Cer(d18:1/18:0), 8_9-DHET/AA, 5-HETE/PC 16:0/20:3, 8_9-DHET/Cer(d18:1/24:1), 8_9-DHET/CE 16:1, 11-HETE/12-HETE, 8_9-DHET/Cer(d18:1/20:0), 8_9-DHET/PC 16:0/20:3 and 8_9-DHET/Cer(d18:1/18:0), and
(c) adjusting treatment of the statin and/or the lipid lowering drug in the subject who is determined to require adjustment based on the one or more lipid concentrations determined in step (a) or the one or more lipid-lipid concentration ratios determined in step (b).

3. The method of claim 2, wherein the adjustment of said treatment with the statin and/or the lipid lowering drug comprises:
(a) a reduction of statin dose;
(b) a cessation of statin treatment;
(c) a re-commencement of statin treatment;
(d) a change to a different statin drug;
(e) a change to a different lipid lowering drug; or
(f) a cessation of another drug treatment which led to muscle toxicity due to its interaction with one or more statins.

4. The method of claim 1, wherein the statin-induced muscle toxicity and/or one or more of its complications is(are) induced by a novel statin or a novel lipid lowering medication.

5. The method of claim 1 or 2, wherein
(a) said subject is being treated with one or more statins;
(b) said subject had undergone statin treatment, but discontinued said treatment due to onset of muscle pain; or
(c) said subject has not yet been treated with statins.

6. The method of claim 1 or 2, wherein the subject is at a high risk for developing statin-induced muscle toxicity and/or one or more of its complications.

7. The method of claim 2, wherein said control to which comparison is made is:
(a) a control sample from the same subject undergoing statin treatment prior to the onset of muscle toxicity;
(b) a control sample from the same subject prior to statin treatment or during discontinuation of statin treatment;
(c) a control sample from a subject with no signs or history of statin-induced muscle toxicity;
(d) a control sample from a population of subjects with no signs or history of statin-induced muscle toxicity;
(e) a control value established from one or more subject(s) not on statin treatment and with no signs or history of muscle toxicity; or
(f) a control value established from one or more subject(s) on statin treatment and with no signs or history of muscle toxicity.

8. The method of claim 1 or 2, further comprising determining or evaluating the level of creatine kinase in said subject or in a sample from said subject, optionally wherein the subject has or does not have elevated creatine kinase levels.

9. The method of claim 1 or 2, wherein
(a) the sample is blood plasma, blood serum, a lipoprotein fraction of blood or muscle biopsy tissue; and/or
(b) the concentration of the one or more lipids or the one or more lipid ratios is determined by using mass spectrometry, nuclear magnetic resonance spectroscopy, fluorescence spectroscopy or dual polarisation interferometry, a high performance separation method such as HPLC or UPLC, an immunoassay such as an ELISA and/or with a binding moiety capable of specifically binding the analyte.

10. A method of determining whether to treat a subject with a statin and/or a lipid lowering drug, wherein the subject is at risk to develop or is suffering from atherosclerosis or cardiovascular disease (CVD) and/or one or more of their complications, the method comprising:

(a) assaying a sample from said subject to determine the concentration of one or more lipids, wherein an increased or decreased concentration in said sample, when compared to a control, is indicative of said subject being at risk of developing or suffering from statin-induced muscle toxicity and/or complication(s) thereof, wherein the one or more lipids whose increase in concentration is compared to the control is selected from: 12-HETE, 15-HETE, 13-HODE, PE P-18:0/20:4, PE O-18:1/20:4, LacCer(d18:1/22:0), LacCer(d18:1/20:0), PE 18:0/20:4, Cer(d18:1/18:0), LacCer(d18:1/24:0), Cer(d18:1/20:0), PC16:0/20:3, AA, Cer(d18:1/24:1), Cer(d18:1/26:1), Glc/GalCer(d18:1/24:1), Cer (d18:1/22:0), Glc/GalCer(d18:1/18:0), Cer(d18:1/16:0), LacCer(d18:1/24:1), SM (d18:1/14:0) (d18:1/13:1-OH), LacCer(d18:1/16:0), CE 18:3 and PC 16:0/20:4, and wherein the one or more lipids whose decrease in concentration is compared to the control is selected from 11_12-DHET, 14_15-DHET, 5-HETrE, 5-HETE and 8_9-DHET; or (b) assaying a sample from said subject to determine the concentration of one or more lipid-lipid concentration ratios, wherein an increased or decreased concentration in said sample, when compared to a control, is indicative of said subject being at risk of developing or suffering from statin -induced muscle toxicity and/or complication(s) thereof, wherein the one or more lipid-lipid concentration ratios whose increase in concentration is compared to the control is selected from: 12-HETE/5-HETrE, 12-HETE/8_9-DHET, 12-HETE/5-HETE, 12-HETE/14_15-DHET, 12-HETE/CE 20:4, 12-HETE/15-HETrE, 12-HETE/LPC 16:0, 15-HETE/8_9-DHET, 12-HETE/5-HEPE, 12-HETE/PC 18:0/18:2, 12-HETE/CK, 15-HETE/5-HETE, 12-HETE/CE 18:3, 13-HODE/8_9-DHET and 15-HETE/15-HETrE; and wherein the one or more lipid-lipid concentration ratios whose decrease in concentration is compared to the control is selected from: 11_12-DHET/CE 18:2, 14_15DHET/CE 18:2, 11_12-DHET/LacCer(d18:1/24:0), 11_12-DHET/Cer(d18:1/16:0), 5-HETE/CE 20:4, 14_15-DHET/LacCer(d18:1/22:0), 14_15-DHET/Glc/GalCer(d18:1/18:0), 15-HETrE/LacCer(d18:1/22:0), 11_12-DHET/Cer(d18:1/20:0), 5-HETE/CE 18:2, 5-HETE/CE 18:1, 8_9-DHET/CE 18:2, 8_9-DHET/CE 18:1, 8_9-DHET/CE 22:6, 14_15-DHET/Cer(d18:1/18:0), 5-HETE/LacCer(d18:1/24:1), 8_9-DHET/CE 16:0, 5-HETE/Glc/GalCer(d18:1/18:0), 8_9-DHET/Cer(d18:1/26:0), 8_9-DHET/LacCer(d18:1/16:0), 5-HETE/9-HODE, 8_9-DHET/Cer(d18:1/16:0), 8_9-DHET/Cer(d18:1/26:1), 8_9-DHET/Glc/GalCer(d18:1/18:0), 11_12-DHET/12-HETE, 8_9-DHET/9-HODE, 5-HETE/Cer(d18:1/18:0), 8_9-DHET/AA, 5-HETE/PC 16:0/20:3, 8_9-DHET/Cer(d18:1/24:1), 8_9-DHET/CE 16:1, 11-HETE/12-HETE, 8_9-DHET/Cer(d18:1/20:0), 8_9-DHET/PC 16:0/20:3 and 8_9-DHET/Cer(d18:1/18:0), and (c) administering the statin or the lipid lowering drug to the subject who has been identified as not being at risk to develop or as suffering from statin-induced muscle toxicity based on the one or more lipid concentrations determined in step (a) or the one or more lipid-lipid concentration ratios determined in step (b).

11. The method of claim 1, wherein the subject:
(a) is being treated with a statin, and said statin is selected from atorvastatin, cerivastatin, fluvastatin, fluvastatin XL, lovastatin, pitavastatin, pravastatin, rosuvastatin and/or simvastatin; and/or
(b) the muscle toxicity is associated with a muscle disease.

12. The method of claim 2, wherein:
(a) said statin is selected from atorvastatin, cerivastatin, fluvastatin, fluvastatin XL, lovastatin, pitavastatin, pravastatin, rosuvastatin and/or simvastatin; and/or
(b) the muscle toxicity is associated with a muscle disease.

13. The method of claim 2, wherein said lipid lowering drug is selected from a HMG-CoA reductase inhibitor, niacin (nicotinic acid), a cholesterol absorption inhibitor, a cholesteryl ester transfer protein (CETP) inhibitor, a bile acid sequestrant; a fibrate or a phytosterol.

14. The method of claim 11 or 12, wherein the muscle disease is a muscle dystrophy.

15. The method of claim 13, wherein the cholesterol absorption inhibitor is ezetimibe or SCH-48461; said cholesteryl ester transfer protein (CETP) inhibitor is torcetrapib, anacetrapib or dalcetrapib; said bile acid sequestrant is colesevelam, cholestyramine or colestipol; and said fibrate is fenofibrate, gemfibrozil, clofibrate, or bezafibrate.

* * * * *